US008546435B2

(12) United States Patent
Aicher et al.

(10) Patent No.: US 8,546,435 B2
(45) Date of Patent: Oct. 1, 2013

(54) TRIAZOLE DERIVATIVES WITH IMPROVED RECEPTOR ACTIVITY AND BIOAVAILABILITY PROPERTIES AS GHRELIN ANTAGONISTS OF GROWTH HORMONE SECRETAGOGUE RECEPTORS

(75) Inventors: Babette Aicher, Frankfurt am Main (DE); Gilbert Mueller, Frankfurt am Main (DE); Klaus Paulini, Maintal (DE); Lars Blumenstein, Frankfurt am Main (DE); Peter Schmidt, Schoeneck (DE); Matthias Gerlach, Brachttal (DE); Michael Teifel, Weiterstadt (DE); Jean Martinez, Caux (FR); Jean-Alain Fehrentz, St. Nazaire de Pezan (FR); Anne-Laure Blayo, Credin (FR)

(73) Assignees: AEterna Zentaris GmbH, Frankfurt am Main (DE); Centre National de la Recherche Scientifique, Paris (FR); University of Montpellier I, Montpellier (FR); University of Montpellier II, Montpellier (FR)

( * ) Notice: Subject to any disclaimer, the term of this patent is extended or adjusted under 35 U.S.C. 154(b) by 152 days.

(21) Appl. No.: 13/235,116

(22) Filed: Sep. 16, 2011

(65) Prior Publication Data
US 2012/0083494 A1   Apr. 5, 2012

Related U.S. Application Data

(60) Provisional application No. 61/383,392, filed on Sep. 16, 2010.

(30) Foreign Application Priority Data

Sep. 16, 2010   (EP) .................................... 10177105

(51) Int. Cl.
*A61K 31/41*   (2006.01)
*C07D 249/08*   (2006.01)

(52) U.S. Cl.
USPC ....................... 514/383; 548/262.2

(58) Field of Classification Search
USPC ....................... 514/383; 548/262.2
See application file for complete search history.

(56) References Cited

U.S. PATENT DOCUMENTS

| 7,829,724 | B2 | 11/2010 | Perrissoud et al. |
| 2007/0037857 | A1 | 2/2007 | Perrissoud et al. |
| 2007/0259854 | A1 | 11/2007 | Murakami et al. |
| 2009/0042905 | A1 | 2/2009 | Perrissoud et al. |
| 2009/0239877 | A1 | 9/2009 | Fehrentz et al. |
| 2010/0331343 | A1 | 12/2010 | Perrissoud et al. |

FOREIGN PATENT DOCUMENTS

| EP | 0 074 229 A1 | 3/1983 |
| EP | 1 790 641 A1 | 5/2007 |
| EP | 1 958 631 A1 | 8/2008 |
| WO | WO 00/54729 | 9/2000 |
| WO | WO 2007/020013 A2 | 2/2007 |
| WO | WO 2009/115503 A1 | 9/2009 |
| WO | WO 2010/051447 A1 | 5/2010 |

OTHER PUBLICATIONS

Moulin, et al., J. Med. Chem., 2007, 50, pp. 5790-5806.*
European Search Report issued May 17, 2011, in Application No. EP 10 17 7105.
Luc Demange, et al., "Synthesis and Pharmacological in Vitro and in Vivo Evaluations of Novel Triazole Derivatives as Ligands of the Ghrelin Receptor 1", Journal of Medical Chemistry, vol. 50, No. 8, XP002504163, Jan. 1, 2007, pp. 1939-1957.
Aline Moulin, et al., "Toward Potent Ghrelin Receptor Ligands Based on Trisubstituted 1,2,4-Triazole Structure. 2. Synthesis and Pharmacological in Vitro and in Vivo Evaluations", Journal of Medical Chemistry, vol. 50, No. 23, XP002620541, Nov. 2007, pp. 5790-5806.
Christopher A. Lipinski, et al., "Bioisosteric Prototype Design of Biaryl Imidazolyl and Triazolyl Competitive Histamine $H_2$-Receptor Antagonists", Journal of Medical Chemistry, vol. 29, No. 11, (American Chemical Society), XP-002260193, Jan. 1, 1986, pp. 2154-2163.
L. L. Grechishkin, et al., "Effect of Derivatives of 3-(β-Aminoethyl)-1,2,4-Triazole on the Histamine $H_1$ —and $H_2$-Receptors", Pharmacology 15, (XP002637212), 1977, pp. 512-518, English Abstract attached.

* cited by examiner

*Primary Examiner* — Susannah Chung
(74) *Attorney, Agent, or Firm* — Oblon, Spivak, McClelland, Maier & Neustadt, L.L.P.

(57) ABSTRACT

The present invention provides novel triazole derivatives with improved receptor activity and bioavailability properties as ghrelin analogue ligands of growth hormone secretagogue receptors according to formula (I) that are useful in the treatment or prophylaxis of physiological and/or pathophysiological conditions in mammals, preferably humans, that are mediated by GHS receptors. The present invention further provides GHS receptor antagonists and agonists that can be used for modulation of these receptors and are useful for treating above conditions, in particular alcohol disorder, drug abuse, growth retardation, cachexia, short-, medium-, and/or long term regulation of energy balance, short-, medium-, and/or long term regulation (stimulation and/or inhibition) of food intake, intake of rewarding food, adipogenesis, adiposity and/or obesity, body weight gain and/or reduction, diabetes, diabetes type I, diabetes type II, tumor cell proliferation, inflammation, inflammatory effects, gastric postoperative ileus, postoperative ileus and/or gastrectomy (ghrelin replacement therapy).

6 Claims, No Drawings

TRIAZOLE DERIVATIVES WITH IMPROVED RECEPTOR ACTIVITY AND BIOAVAILABILITY PROPERTIES AS GHRELIN ANTAGONISTS OF GROWTH HORMONE SECRETAGOGUE RECEPTORS

CROSS REFERENCE TO RELATED APPLICATIONS

The present application is a utility application based on U.S. Provisional Application Ser. No. 61/383,392, filed on Sep. 16, 2010, and claims the benefit of the filing date of European Application No. 10177105.3, also filed on Sep. 16, 2010, the text of each of which is also incorporated by reference.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

REFERENCE TO A "SEQUENCE LISTING," A TABLE, OR A COMPUTER PROGRAM LISTING APPENDIX SUBMITTED ON A COMPACT DISC AND AN INCORPORATION-BY-REFERENCE OF THE MATERIAL ON THE COMPACT DISC

Not Applicable

BACKGROUND OF THE INVENTION

1. Field of the Invention

The invention relates to novel triazole derivatives with improved receptor activity and bioavailability properties that act as ghrelin analogous ligands of growth hormone secretagogue receptors. These compounds are useful in modulating growth hormone plasma levels in mammals as well as in the treatment and/or regulation of various physiological and pathophysiological conditions, such as growth retardation, obesity, food intake, energy balance, and other metabolic disorders, tumor cell proliferation, wound/burn/bone healing, inflammation, and addiction processes like food reward, alcohol-related disorders and drug abuse.

2. Description of the Related Art

Ghrelin, a 28 amino acid peptide with a unique octanoyl modification on Ser-3 (Kojima M et al., Nature 1999, 402: 656-660), was identified as an endogenous ligand for the growth hormone secretagogue receptor type 1a (GHS-R 1a), a G-protein coupled receptor (Howard A D et al., Science 1996, 273: 974-977). Ghrelin is essentially produced in the upper intestinal tract/stomach but lower amounts were also detected in bowel, pancreas, kidney, the immune system, placenta, testes, pituitary, lung and in the hypothalamus (van der Lely A J et al., Endocrine Rev. 2004, 25: 426-457; Cowley M et al., Neuron 2003, 37: 649-661).

In humans, ghrelin stimulates growth hormone (GH) via a pathway independent from GHRH receptor and in synergy with GHRH on GH secretion (Arvat E et al., J. Clin. Endocrinol. Metab. 2001, 86: 1169-1174). Besides, it also stimulates ACTH, prolactin, cortisol, aldosterone and epinephrine secretion (Arvat E et al., J. Clin. Endocrinol. Metab. 2001, 86: 1169-1174; Nagaya N et al., Am. J. Physiol. Regul. Integr. Comp. Physiol. 2001, 280: R1483-1487; Takaya K et al., J. Clin. Endocrinol. Metab. 2000, 85: 4908-4911).

Ghrelin is thought to participate in metabolism regulation and energy expenditure, so ghrelin expression and secretion into the general circulation from the stomach is expected to be influenced by metabolic hormones. In obese humans, plasma ghrelin levels are reduced, suggesting that the elevated insulin or leptin levels of obese subjects lower ghrelin secretion (Tschop M et al, Diabetes 2001, 50: 707-709).

The release of growth hormone in humans and animals is believed to treat physiological or pathophysiological conditions characterized by a deficiency in growth hormone secretion as well as to treat those conditions which are improved by the anabolic effects of growth hormone.

Initially, clinical applications with GH were limited to treatment of GH-deficient children, but the commercialization of recombinant human growth hormone (rhGH) allowed many studies which showed other potential clinical uses of GH (Strobl J S et al., Pharmacol. Rev. 1994, 46: 1-34; Torosian M H, J. Pediatr. Endocrinol. 1993, 6: 93-97). rhGH has shown promise in the treatment of patients with burns, wounds, bone fractures and more recently in reversing the catabolic effects of glucocorticoids, chemotherapy and AIDS as well as in modifying body composition (Rudman D et al., N. Engl. J. Med. 1990, 323: 1-6; Papadakis M A et al., Ann. Intern. Med. 1996, 124: 708-716; Welle S et al., J. Clin. Endocrinol. Metab. 1996, 81: 3239-3243).

GH, synthesized and stored in the pituitary gland, is released under the control of two known hypothalamic hormones: growth hormone releasing hormone (GHRH) and the inhibitory hormone somatostatin (SRIF). In most cases, GH deficiency is related to a hypothalamic defect and not to a pituitary deficiency in GH. Therefore, as an alternative treatment to rhGH, GH-deficient patients could also be treated with any compound that releases endogenous GH from the pituitary gland. This can either be performed with GHRH which stimulates GH release but also with synthetic growth hormone secretagogues (GHS).

Many synthetic, peptidyl and non-peptidyl GHS, such as GHRPs 1, 2 and 6, Hexarelin, MK-0677, EP-01572, were shown to specifically bind to the then orphan receptor "GHS receptor"—several of them long before ghrelin and ghrelin/GHS receptor were discovered (see "Camanni F et al., Front Neuroendocrinol. 1998, 19: 47-72"; "Casanueva F F et al., Trends Endocrinol. Metab. 1999, 10: 30-38"; "van der Lely A J et al., Endocrine Rev. 2004, 25: 426-457" for further references). GHS also show potent GH releasing action and have the same biological activities as mentioned above for ghrelin.

GHS were also disclosed in the following patents or patent applications (not exhaustive list): U.S. Pat. No. 6,071,926, U.S. Pat. No. 6,329,342, U.S. Pat. No. 6,194,578, US 2001/0041673, U.S. Pat. No. 6,251,902, US 2001/0020012, US 2002/0013320, US 2002/0002137, WO 95/14666, WO 96/15148, WO 01/96300.

While the ghrelin/GHS induced GH secretion is mediated by the activation of the ghrelin/GHS receptor type 1a (GHS-R 1a), there is evidence so far that at least some of the other effects of ghrelin and GHS are also mediated by different receptors of the GHS receptor family or even different binding sites on a given GHS receptor.

GHS receptors are concentrated in the hypothalamus-pituitary area but appear also to be distributed in other central and peripheral tissues (Hattori N et al., J. Clin. Endocrinol. Metab. 2001, 86: 4284-4291; Gnanapavan S et al., J. Clin. Endocrinol. Metab. 2002, 87: 2988-2991; Muccioli G et al., J. Endocrinol. 2000, 157: 99-106; Muccioli G et al., Ann. Endocrinol. 2000, 61: 27-31; Muccioli G et al., Eur. J. Pharmacol.

2002, 440: 235-254; Papotti M et al., J. Clin. Endocrinol. Metab. 2000, 85: 3803-3807; Cassoni P et al., J. Clin. Endocrinol. Metab. 2001, 86: 1738-1745; Guan X M et al., Brain Res. Mol. Brain. Res. 1997, 48: 23-29; Bluet-Pajot M T et al., Endocrine 2001, 14: 1-8; Korbonits M et al., J. Clin. Endocrinol. Metab. 1998, 83: 3624-3630).

Two GHS type 1 receptors have been identified, GHS-R 1a and GHS-R 1b, that in human are presumably expressed by a single gene and alternatively spliced (van der Lely A J et al., Endocrine Rev. 2004, 25: 426-457; Howard A D et al., Science 1996, 273: 974-977; Smith R G et al., Endocr. Rev. 1997, 18: 621-645; Smith R G et al., Endocrine 2001, 14: 9-14; McKee K K et al., Mol. Endocrinol. 1997, 11: 415-423; Petersenn S, Minerva Endocrinol. 2002; 27: 243-256). Among mammalian species a high degree of sequence identity has been reported for GHS-R 1a (Petersenn S, Minerva Endocrinol. 2002; 27: 243-256: between 91.8% and 95.6%).

Motilin receptor, was discovered as a member of the GHS receptor family, having 52% identity (Smith R G et al., Endocrine 2001, 14: 9-14; McKee K K et al., Genomics 1997, 46: 426-434). Gastrointestinal motilin receptor 1a and GHS-R 1a show a high similarity (Smith R G et al., Endocrine 2001, 14: 9-14; Feighner S D et al., Science 1999, 284: 2184-2188).

Other GHS receptor family members appear to be neurotensin receptor, TRH receptor, GPR38 (FM1), GPR39 (FM2) and FM3 (Smith R G et al., Endocr. Rev. 1997, 18: 621-645; Smith R G et al., Horm. Res. 1999, 51 (Suppl. 3): 1-8; Tan C P et al., Genomics 1998, 52: 223-229; Howard A D et al., Science 1996, 273: 974-977). Further GHS receptor subtypes appear to exist in a wide variety of central and peripheral tissues (van der Lely A J et al., Endocrine Rev. 2004, 25: 426-457). For instance, a cardiac GHS-R has been reported (Bodart V et al., Circ. Res. 1999, 85: 796-802) with a predicted sequence similar to that of CD36, a multifunctional receptor known as glycoprotein IV (Bodart V et al., Circ. Res. 2002, 90: 844-849). Cassoni et al. (J. Clin. Endocrinol. Metab. 2001, 86: 1738-1745) report the existence of GHS-R subtypes in neoplastic mammary cells that are activated by ligands binding to specific binding sites different from the classical GHS-R type 1. Furthermore, data gathered by these authors support the hypothesis that even different binding site subtypes do exist for GHS-R in peripheral organs, which are possibly due to their endocrine or non-endocrine, but also on their normal or neoplastic nature.

The ubiquity of GHS binding sites explains that independently from their strong growth hormone secretagogue properties, ghrelin as well as synthetic GHS are implicated in several important physiological and pathophysiological conditions.

Accordingly, potential clinical applications include among others a) Short-, Medium- and Long-Term Regulation of Energy Balance and/or Food Intake (Tschoep M et al., Nature 2000, 407: 908-913; Asakawa A et al., Gut 2003, 52: 947-952; US 2001/0020012; Kojima M et al., Curr. Opin. Pharmacol. 2002, 2: 665-668; Horvath T L et al., Curr. Pharm. Des. 2003, 9: 1383-1395; Wren A M et al., J. Clin. Endocrinol. Metab. 2001, 86: 5992-5995)

Expression of GHS-R1a has been shown on neurons of hypothalamus paraventricular nucleus. These neurons send efferents onto key hypothalamic circuits for the control of food intake, like the arcuate nucleus which produces the mediator NPY. It is thought that the stimulation of food intake by ghrelin and/or GHS is mediated by an increase of NPY in the arcuate nucleus (Willesen M G et al., Neuroendocrin. 1999, 70: 306-316). Single administration (icv or ip) of anti-ghrelin IgG suppressed acute feeding in lean rats (Bagnasco M et al., Regul. Pept. 2003, 111: 161-167). Chronic twice-daily icv administration of anti-ghrelin IgG reduced body weight over a five-day period (Murakami N et al., J. Endocrinol. 2002, 174: 283-288).

A recent study using a peptidic GHS-R 1a antagonist, [D-Lys-3]-GHRP-6, showed a reduction of food intake and body weight gain in diet induced obese mice (Asakawa A et al., Gut, 2003, 52: 947-952). The fact that peptidyl compounds, initially characterized as growth hormone secretagogues, are able to stimulate selectively food intake in rats without inducing growth hormone secretion, suggests the existence of a GHS-R subtype different from GHS-R 1a in the hypothalamus (Torsello A et al., Neuroendocrin. 2000, 72: 327-332; Torsello A et al., Eur. J. Pharmacol. 1998, 360: 123-129).

b) Treatment of Adipogenesis, Adiposity and/or Obesity and Reduction of Body Weight (Tschop M et al., Nature 2000, 407: 908-913; Asakawa A et al., Gut 2003, 52: 947-952)

Chronic administration of ghrelin and/or GHS in freely feeding mice and rats results in increased body weight and decreased fat utilization (Tschop M et al., Nature 2000, 407: 908-913). Furthermore, it has been reported that ghrelin and des-octanoyl ghrelin promote adipogenesis in vivo (Thompson N M et al., Endocrinol. 2004, 145: 234-242) and inhibit isoproterenol-induced lipolysis in rat adipocytes via a non-type GHS-R 1a (Muccioli G et al., Eur. J. Pharmacol. 2004, 498: 27-35). On the other hand, there is also a report describing that the expression of the GHS-R1a in rat adipocytes increases with age and during adipogenesis (Choi K et al., Endocrinol. 2003, 144, 754-759).

c) Treatment of Tumor Cell Proliferation

As in the case for other members of the hypothalamus-pituitary axis which regulates the secretion of growth hormone, evidence is emerging to indicate that ghrelin and GHS-receptors may play an important autocrine/paracrine role in some cancers (Jeffery P L et al., Cytokine Growth Factor Rev. 2003, 14: 113-122). Specific binding sites for ghrelin, peptidyl- and non-peptidyl GHS are present in tumoral tissues, like prostate cancer cell line PC3 (Jeffery P L et al., J. Endocrinology 2002, 172: R7-R11), thyroid tissue (Cassoni P et al., J. Endocrinol. 2000, 165: 139-146), lung carcinoma cells CALU-1 (Ghé C et al., Endocrinol. 2002, 143: 484-491) and breast carcinomas (Cassoni P et al., J. Clin. Endocrinol. Metab. 2001, 86: 1738-1745).

In the case of breast, the specific binding sites for GHS were found in tumoral tissue while the normal mammary parenchyma did not reveal such receptors. Synthetic GHS have been reported to inhibit the proliferation of lung carcinoma cells CALU-1 (Ghé C et al., Endocrinol. 2002, 143: 484-491) and that of breast carcinoma cell lines (Cassoni P et al., J. Clin. Endocrinol. Metab. 2001, 86: 1738-1745).

Both ghrelin and non-acylated ghrelin bind to tumoral tissues. Because non-acylated ghrelin is unable to bind the GHS-R 1a, it is likely that the binding site of GHS to tumoral tissues is different from the GHS-R 1a. From these data, one can anticipate that the binding site in tumoral tissues recognizes ligands of the GHS-R 1a and in addition other not yet characterized chemical structures. Synthetic ligands of GHS-R1a may have therefore the potential to inhibit the proliferation of tumor cells expressing subtypes of GHS receptors.

d) Treatment of Inflammation/Anti-Inflammatory Effects

The anti-inflammatory effect of the ghrelin agonist growth hormone-releasing peptide-2 (GHRP-2) in chronic arthritis with clinical manifestations of hypermetabolism and cachexia was demonstrated (Granado M et al., Am. J. Physiol. Endocrinol. Metab. 2005, 288: E486-492). These data suggest that the anti-inflammatory action of GHRP-2 is mediated by activation of ghrelin receptors expressed by immune competent cells.

e) Treatment of Cachexia

The anti-cachetic effect of administered recombinant growth hormone in an animal model of chachexia (Roubenoff R et al., Arthritis Rheum. 1997, 40(3): 534-539) could be demonstrated (Ibanez de Caceres I et al., J. Endocrin. 2000, 165(3): 537-544). The findings are also in line with data of patients with rheumatoid arthritis (Roubenoff R et al., J Clin Invest. 1994, 93(6): 2379-2386).

f) Treatment of Gastrectomy (Ghrelin Replacement Therapy)

The gastric hormone ghrelin was given to mice subjected to gastrectomy or sham operation (Dornonville de la Cour C et al., Gut 2005, 54(7): 907-913). The results presented show that ghrelin replacement therapy at least partially reverse gastrectomy induced reduction in body weight and body fat.

g) Treatment of (Gastric) Postoperative Ileus

The effect of ghrelin on the motor function of the gastrointestinal tract in rat was evaluated. It could be shown that ghrelin reverses the delayed gastric evacuation and is a strong prokinetic agent useful for the treatment/reversion of postoperative gastric ileus (Trudel L et al., Am J Physiol Gastrointest Liver Physiol 2002, 282(6): G948-G952).

h) Treatment of Diabetes (Diabetes Type I and Type II)

The effect of ablation of ghrelin in leptin-deficient mice was studied (Sun et al., Cell Metabolism 2006, 3: 379-386). The results show that deletion of ghrelin augments insulin secretion in response to glucose challenge indicating that inhibition of ghrelin or counteracting its activity may be a possible way for the treatment of diabetes including its subtypes I and II (see also WO 03/051389).

i) Treatment of Addiction Processes Like Food Reward, Alcohol Disorders, and Drug Abuse The mesolimbic dopamine projections, originating from neuronal cell populations in the ventral tegmental area (VTA) and terminating in the ventral striatum and the prefrontal cortex, are linked to anticipatory, appetitive or approach phases of motivated behaviour and are important for anticipatory food reward and food seeking behaviours (Bassareo and Chiara 1999, Neuroscience 89, 637-641; Richardson and Gratton 1998, J Neurosci 18, 9130-9138). Activation of these dopamine projections is also elicited by ingestion of rewarding foods as well as by other rewards, both natural (e.g. sex) and artificial, like alcohol and drug abuse (Berridge and Robinson 1998, Brain Res Brain Res Rev 28, 637-641). There is accumulating evidence that the mesolimbic system is a target for ghrelin. In addition to the hypothalamus, the ghrelin receptor has also been identified in the ventral tegmental area (VTA) and laterodorsal tegmental area (LDTg). More recent findings indicate that the effects of ghrelin on food intake are partly mediated by the mesolimbic dopamine systems involved in reward-seeking behaviour (Jerlhag E. et al. 2006 Addiction Biology 11:45-54; Jerlhag E, et al. Addict Biol. 2007 12:6-16; Egecioglu E. et al. 2010, Addiction Biology 15, 304-311). In addition, most recent data confirm the suitability of ghrelin antagonists for the treatment of alcohol disorders (WO2009/020419 and Jerlhag et al. 2009. PNAS 106, 11318-11323) and drug abuse (Jerlhag E. et al. 2010, Psychopharmacology 211, 415-422).

Further fields of application comprise acceleration of recovery of patients having undergone major surgery (e.g. U.S. Pat. No. 6,194,578); accelerating the recovery of burn patients (e.g. U.S. Pat. No. 6,194,578); attenuating protein catabolic response after a major operation (e.g. U.S. Pat. No. 6,194,578); reducing cachexia and protein loss due to acute or chronic illness (e.g. U.S. Pat. No. 6,194,578); treating central nervous system disorders of patients undergoing a medical procedure in combination with antidepressants (e.g. US 2002/0002137 A1); acceleration of bone fracture repair and cartilage growth (e.g. U.S. Pat. No. 6,194,578); treatment or prevention of osteoporosis; stimulation of the immune system; accelerating wound healing (e.g. U.S. Pat. No. 6,194,578); treatment of growth retardation associated with the Prader-Willi syndrome, Turner's syndrome and obesity; treatment of intrauterine growth retardation, skeletal dysplasia, hypercortisolism and Cushing's syndrome; treatment of osteochondrodysplasias, Noonan's syndrome, schizophrenia, depressions and Alzheimer's disease; treatment of pulmonary dysfunction and ventilator dependency; treatment of hyperinsulinemia including nesidioblastosis; adjuvant treatment for ovulation induction; prevention of the age-related decline of thymic function; improvement in muscle strength and mobility (e.g. U.S. Pat. No. 6,194,578); maintenance of skin thickness (e.g. U.S. Pat. No. 6,194,578); improvement of sleep quality (e.g. U.S. Pat. No. 6,071,926); prevention of congestive heart failure alone (e.g. U.S. Pat. No. 6,329,342; U.S. Pat. No. 6,194,578) and in combination with corticotropin releasing factor antagonists (e.g. US 2001/0041673); metabolic homeostasis or renal homeostasis (e.g. in the frail elderly)(e.g. U.S. Pat. No. 6,194,578); improving glycemic control (e.g. U.S. Pat. No. 6,251,902); treatment of systemic lupus erythematosus and inflammatory bowel disease (e.g. US 2002/0013320); treating or preventing frailty associated with aging or obesity (e.g. U.S. Pat. No. 6,194,578); as well as stimulation of osteoblasts.

Animals were not forgotten in potential applications such as stimulation of food intake (Wren A M et al., Diabetes 2001, 50: 2540-2547), stimulation of the immune system in companion animals and treatment of disorder of aging, growth promotion in livestock and stimulation of wool growth in sheep.

Compounds containing triazole moieties have been widely recognized in the medicinal chemistry due to their various biological activities. The following patent families are all directed to heterocyclic compounds that are said to show certain biological action for use in different medicinal indications. Triazole moieties are implicitly or explicitly contained.

Triazole derivatives as Ghrelin Analogue Ligands of Growth Hormone Secretagogue Receptors having good receptor affinity are disclosed in WO07/020013.

WO 2004/111015 discloses modulators of the glucocorticoid receptor. WO 2004/052280 describes anti-angiogenic compounds as inhibitors of tyrosine kinase activity of VEGF receptors and their use in cancer. WO 2004/096795 also discloses tyrosine kinase inhibitors, preferably C-FMS inhibitors. WO 03/011831 and WO 03/011210 both describe heteroarylheteroalkylamine derivatives as inhibitors of nitric oxide synthase. WO 02/00651 is directed to Factor XA inhibitors for use in thromboembolic disorders. WO 01/94318 and WO 01/94317 both describe chemical libraries of substituted azole derivatives and methods of their synthesis for use in drug discovery high-throughput screening. However, they fail to provide any biological activity or any medicinal use nor do they name specific compounds. WO 00/76971 and WO 00/76970 both claim serine protease inhibitors useful as antithrombotic agents. WO 01/36395 discloses triazole derivatives as farnesyl transferase inhibitors. WO 96/33176 and U.S. Pat. No. 5,703,092 are directed to hydroxamic acid compounds as metalloprotease and TNF inhibitors. WO 93/09095 describes 2-heterocyclicethylamine derivatives and their use in neurological and neurodegenerative disorders. WO 2004/103270 claims compounds for the treatment of thrombosis, in particular Factor XIa inhibitors. WO 98/38177, U.S. Pat. No. 6,506,782, U.S. Pat. No. 6,849,650 and US 2003/0130188 all describe heterocyclic compounds as inhibitors of beta-amyloid peptide release or its synthesis for use in Alzheimer's disease.

Heterocyclic compounds that may be useful as GHS have also been described in the literature.

WO 00/54729, for instance, discloses heterocyclic aromatic compounds as GH secretagogues which are said to stimulate endogenous production and/or release of GH and can also contain triazole moieties. In addition, a method for increasing levels of endogenous GH or increasing the endogenous production or release of GH administering such GHS is described. Furthermore, a method is provided for preventing or treating osteoporosis (improving bone density and/or strength), or treating obesity, or increasing muscle mass and/or muscle strength and function in elderly humans, or reversal or prevention of frailty in elderly humans administering such GHS.

However, although claiming in vivo GH release, WO 00/54729 fails to actually prove such effect. Neither in vitro nor in vivo data are contained that demonstrate any stimulation of or increase in endogenous production and/or release of GH.

Besides, WO 00/54729 fails to describe and show action of those claimed compounds on any biological target, i.e. claimed compounds are not shown/described to be ligands of one or more specific receptors, for instance of a receptor family, that bind to them and modulate their activity.

Furthermore, WO 00/54729 fails to describe and demonstrate inhibitory and/or antagonistic activity of claimed compounds. As a matter of fact, such compounds are not shown to decrease levels of endogenous GH and/or inhibit or decrease endogenous production and/or release of GH. Nor is an inhibitory action on any receptor mentioned nor made obvious.

U.S. Pat. No. 6,525,203, U.S. Pat. No. 6,518,292 U.S. Pat. No. 6,660,760 are members of the same patent family as WO 00/54729 that, however, do not comprise triazole moieties as claimed subject matter any more. With regard to biological activity, the above stated facts as for WO 00/54729 apply.

WO 2004/021984 describes heterocyclic aromatic compounds GH secretagogues which are said to be useful in stimulating endogenous production or release of GH. However, claimed compounds consists of bi- to tetracylic aromatic rings and do not contain triazoles.

Analogous to WO 00/54729 in vivo GH release is claimed, but neither in vitro nor in vivo data are contained that demonstrate any stimulation of or increase in endogenous production and/or release of GH. With regard to biological activity, the same stated facts as for WO 00/54729 apply.

WO 97/23508 claims compounds of peptide mimetic nature as GHS and are said to act directly on pituitary cells in vitro to release GH therefrom and show improved properties, such as improved resistance to proteolytic degradation and improved bioavailability. In addition, claimed compounds could also be administered in vivo to increase GH release. The compounds are peptide derivatives and do not explicitly contain triazole moieties.

However, once again and in analogy to above WO 00/54729 and WO 2004/021984, WO 97/23508 fails to exhibit any in vitro or in vivo data that demonstrate the claimed effects such as direct action on pituitary cells, GH release therefrom and improved properties. Furthermore, with regard to biological targets and inhibitory/antagonistic activity, the above stated facts as for WO 00/54729 apply.

U.S. Pat. No. 6,127,391, U.S. Pat. No. 5,977,178 and U.S. Pat. No. 6,555,570 are members of the same patent family as WO 97/23508. The facts as stated for WO 97/23508 do apply.

The compounds described in this invention were designed to exhibit improved activity against ghrelin receptors of at least factor three compared to a representative compound, i.e. compound 50 disclosed in WO07/020,013.

Furthermore, the compounds described in this invention are expected to possess improved oral bioavailability. Chemical synthesis was directed to modify residues R2, R5, and R7 in order to provide compounds with improved ADME properties.

In comparison to the compounds disclosed in WO07/020, 013, the compounds described herein exhibit improved properties in at least one of the following parameters, which are widely accepted to be essential for reasonable oral bioavailability (Caldwell G W. 2000, Curr Opin Drug Discov Devel. 3(1), 30-41; Thomas V H. et al. 2006, Expert Opin Drug Metab Toxicol 2(4), 591-608):

CaCo-2 permeability: $P_{APP}$ (a→b)>1×10$^6$ cm/s

No evidence of efflux as indicated by b→a/a→b ratio<2

Metabolic stability: In in vitro microsomal stability studies, a rat CL of <50 ml/min/kg (alternatively, >30% remaining at 60 min)

BRIEF SUMMARY OF THE INVENTION

Hence, the present invention has the object to provide novel compounds with improved receptor antagonistic activity and ADME properties which can be employed for the treatment of physiological and/or pathophysiological conditions in mammals, in particular humans, that are mediated by GHS receptors. It is another object of the present invention to provide agonists of GHS receptors for those treatments. It is also another object of the underlying invention to provide inverse agonists for the above treatment where the treatment is achieved by modulation of GHS receptors. A further object of the present invention is to provide partial agonists/antagonists of GHS receptors for those treatments.

BRIEF DESCRIPTION OF THE SEVERAL VIEWS OF THE DRAWING

Not Applicable

DETAILED DESCRIPTION OF THE INVENTION

The object of the invention has been surprisingly solved in one aspect by providing compounds according to formula (I)

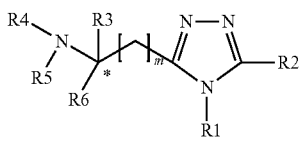
(I)

wherein:

(A)
R1 and R2 are independently of one another selected from the group consisting of "hydrogen atom, alkyl, alkenyl, alkynyl, cycloalkyl, cycloalkylalkyl, aryl, heteroaryl, arylalkyl, heteroarylalkyl, heterocyclyl, heterocyclylalkyl, alkylsulfonyl, arylsulfonyl, arylalkylsulfonyl" which are optionally substituted in the alkyl, cycloalkyl, cycloalkylalkyl, aryl, heteroaryl, arylalkyl, heteroarylalkyl, heterocyclyl and/or heterocyclylalkyl group by up to 3 substituents independently selected from the group consisting of "halogen, —F, —Cl, —Br, —I, —N₃, —CN, —NR7R8, —NR11R12, —OH, —NO₂, alkyl, aryl, heteroaryl, arylalkyl, —O-alkyl, —O-aryl, —O-arylalkyl, —C(O)O-alkyl, —C(O)O-cycloalkyl, —C(O)O-cycloalkylalkyl, —C(O)O-aryl, —C(O)O-arylalkyl, —C(O)O-heteroaryl, —C(O)O-heteroarylalkyl, —C(O)O-heterocyclyl, —C(O)O-heterocyclylalkyl, —C(O)NR9R10, —C(S)NR9R10;";

one of radicals R3 and R4 is a hydrogen atom, whereas the other radical is selected from the group consisting of "hydrogen atom, alkyl, aryl, heteroaryl, arylalkyl, heteroarylalkyl, heterocyclyl, heterocyclylalkyl, -alkyl-O-aryl, -alkyl-O-arylalkyl, -alkyl-O-heteroaryl, -alkyl-O-heteroarylalkyl, -alkyl-O-heterocyclyl, -alkyl-O-heterocyclylalkyl, -alkyl-CO-aryl, -alkyl-CO-arylalkyl, -alkyl-CO-heteroaryl, -alkyl-CO-heteroarylalkyl, -alkyl-CO-heterocyclyl, -alkyl-CO-heterocyclylalkyl, -alkyl-C(O)O-aryl, -alkyl-C(O)O-arylalkyl, -alkyl-C(O)O-heteroaryl, -alkyl-C(O)O-heteroarylalkyl, -alkyl-C(O)O-heterocyclyl, -alkyl-C(O)O-heterocyclylalkyl, -alkyl-CO—NH₂, -alkyl-CO—OH, -alkyl-NH₂, -alkyl-NH—C(NH)—NH₂, alkylsulfonyl, arylsulfonyl, arylalkylsulfonyl, alkyl-S-alkyl, alkyl-S—H" which are optionally substituted in the aryl, heteroaryl, arylalkyl, heteroarylalkyl, heterocyclyl and/or heterocyclylalkyl group by up to 3 substituents independently selected from the group consisting of "halogen, —F, —Cl, —Br, —I, —N₃, —CN, —NR7R8, —OH, —NO₂, alkyl, aryl, arylalkyl, —O-alkyl, —O—CF₃, —O-aryl, —O-arylalkyl";

R5 is selected from the group consisting of "—C(S)alkyl, —C(S)-cycloalkyl, —C(S)-cycloalkylalkyl, —C(S)-aryl, —C(S)-arylalkyl, —C(S)-heteroaryl, —C(S)-heteroarylalkyl, —C(S)-heterocyclyl, —C(S)-heterocyclylalkyl, —C(O)O-alkyl, —C(O)O-cycloalkyl, —C(O)O-cycloalkylalkyl, —C(O)O-aryl, —C(O)O-arylalkyl, —C(O)O-heteroaryl, —C(O)O-heteroarylalkyl, —C(O)O-heterocyclyl, —C(O)O-heterocyclylalkyl, —C(O)NR9R10, —C(S)NR9R10"; which are optionally substituted in the alkyl, cycloalkyl, cycloalkylalkyl, aryl, heteroaryl, arylalkyl, heteroarylalkyl, heterocyclyl and/or heterocyclylalkyl group by up to 3 substituents independently selected from the group consisting of "halogen, —F, —Cl, —Br, —I, —N₃, —CN, —CF₃, —NR7R8, —OH, —NO₂, —NH₂, alkyl, aryl, arylalkyl, —OH, —O-alkyl, —O-aryl, —O-arylalkyl";

R6 is selected from the group consisting of "hydrogen atom, alkyl, cycloalkyl, cycloalkylalkyl";

R7 and R8 are independently of one another selected from the group consisting of "hydrogen atom, alkyl, cycloalkyl, and cycloalkylalkyl";

R9 and R10 are independently of one another selected from the group consisting of "hydrogen atom, alkyl, cycloalkyl, heterocyclyl, aryl, heteroaryl, arylalkyl, and hetararyloalkyl";

R11 is a "hydrogen atom",

R12 is independently of one another selected from the group consisting of "—C(O)H, —C(O)-alkyl; —C(O)-cycloalkyl, —C(O)-cycloalkylalkyl, —C(O)-aryl, —C(O)-arylalkyl, —C(O)-heteroaryl, —C(O)-heteroarylalkyl, —C(O)-heterocyclyl, —C(O)-heterocyclylalkyl", Or (B)
R1 is independently of one another selected from the group consisting of "hydrogen atom, alkyl, alkenyl, alkynyl, cycloalkyl, cycloalkylalkyl, aryl, heteroaryl, arylalkyl, heteroarylalkyl, heterocyclyl, heterocyclylalkyl, alkylsulfonyl, arylsulfonyl, arylalkylsulfonyl" which are optionally substituted in the alkyl, cycloalkyl, cycloalkylalkyl, aryl, heteroaryl, arylalkyl, heteroarylalkyl, heterocyclyl and/or heterocyclylalkyl group by up to 3 substituents independently selected from the group consisting of "halogen, —F, —Cl, —Br, —I, —N₃, —CN, —NR7R8, —OH, —NO₂, alkyl, aryl, arylalkyl, —O-alkyl, —O-aryl, —O-arylalkyl";

R2 is an "alkyl group", which is substituted by up to 2 substituents independently selected from the group consisting of "Aryl, Heteroaryl, —C(O)O-alkyl, —C(O)O-cycloalkyl, —C(O)O-cycloalkylalkyl, —C(O)O-aryl, —C(O)O-arylalkyl, —C(O)O-heteroaryl, —C(O)O-heteroarylalkyl, —C(O)O-heterocyclyl, —C(O)O-heterocyclylalkyl, —C(O)NR9R10, —NR11R12", and in the case of aryl, heteroaryl the alkylgroup has to be in addition substituted with —NR11R12;

one of radicals R3 and R4 is a hydrogen atom, whereas the other radical is selected from the group consisting of "hydrogen atom, alkyl, aryl, heteroaryl, arylalkyl, heteroarylalkyl, heterocyclyl, heterocyclylalkyl, -alkyl-O-aryl, -alkyl-O-arylalkyl, -alkyl-O-heteroaryl, -alkyl-O-heteroarylalkyl, -alkyl-O-heterocyclyl, alkyl-O-heterocyclylalkyl, -alkyl-CO-aryl, -alkyl-CO-arylalkyl, -alkyl-CO-heteroaryl, -alkyl-CO-heteroarylalkyl, -alkyl-CO-heterocyclyl, -alkyl-CO-heterocyclylalkyl, -alkyl-C(O)O-aryl, -alkyl-C(O)O-arylalkyl, -alkyl-C(O)O-heteroaryl, -alkyl-C(O)O-heteroarylalkyl, -alkyl-C(O)O-heterocyclyl, -alkyl-C(O)O-heterocyclylalkyl, -alkyl-CO—NH₂, -alkyl-CO—OH, -alkyl-NH₂, -alkyl-NH—C(NH)—NH₂, alkylsulfonyl, arylsulfonyl, arylalkylsulfonyl, alkyl-S-alkyl, alkyl-S—H" which are optionally substituted in the aryl, heteroaryl, arylalkyl, heteroarylalkyl, heterocyclyl and/or heterocyclylalkyl group by up to 3 substituents independently selected from the group consisting of "halogen, —F, —Cl, —Br, —I, —N₃, —CN, —NR7R8, —OH, —NO₂, alkyl, aryl, arylalkyl, —O-alkyl, —O-aryl, —O-arylalkyl";

R5 is selected from the group consisting of "hydrogen atom, alkyl, cycloalkyl, cycloalkylalkyl, aryl, heteroaryl, arylalkyl, heteroarylalkyl, heterocyclyl, heterocyclylalkyl, —CO-alkyl, —CO-cycloalkyl, —CO-cycloalkylalkyl, —CO-aryl, —CO-arylalkyl, —CO-heteroaryl, —CO-heteroarylalkyl, —CO-heterocyclyl, —CO—heterocyclylalkyl, —CO—C*(R9R10)-NH$_2$, —CO—CH$_2$—C*(R9R10)-NH$_2$, —CO—C*(R9R10)—CH$_2$—NH$_2$, alkylsulfonyl, arylsulfonyl, arylalkylsulfonyl" which are optionally substituted by up to 3 substituents independently selected from the group consisting of "halogen, —F, —Cl, —Br, —I, —N$_3$, —CN, —NR7R8, —OH, —NO$_2$, alkyl, aryl, arylalkyl, —O-alkyl, —O-aryl, —O-arylalkyl";

R6 is selected from the group consisting of "hydrogen atom, alkyl, cycloalkyl, cycloalkylalkyl";

R7 and R8 are independently of one another selected from the group consisting of "hydrogen atom, alkyl, cycloalkyl, cycloalkylalkyl";

R9 and R10 are independently of one another selected from the group consisting of "hydrogen atom, alkyl, natural amino acid side chain, unnatural amino acid side chain";

R11 is a "hydrogen atom";

R12 is independently of one another selected from the group consisting of "—C(O)H, —C(O)-alkyl; —C(O)-cycloalkyl, —C(O)-cycloalkylalkyl, —C(O)-aryl, —C(O)-arylalkyl, —C(O)-heteroaryl, —C(O)-heteroarylalkyl, —C(O)-heterocyclyl, —C(O)-heterocyclylalkyl";

in terms of (A) and (B)

m is 0, 1 or 2; and

* means a carbon atom of R or S configuration when chiral;

that can be used for the manufacture of a medicament for the treatment or prophylaxis of physiological and/or pathophysiological conditions in mammals that are mediated by GHS receptors.

In a further aspect, the object of the invention has surprisingly been achieved by providing novel triazole compounds selected from the group consisting of:

compound 1 [5-{(R)-2-(1H-Indol-3-yl)-1-[(pyridine-3-carbonyl)-amino]-ethyl}-4-(4-methoxy-benzyl)-4H-[1,2,4]triazol-3-yl]-acetic acid ethyl ester;

compound 2 N-[(R)-1-[5-Carbamoylmethyl-4-(4-methoxy-benzyl)-4H-[1,2,4]triazol-b 3-yl]-2-(1H-indol-3-yl)-ethyl]-nicotinamide;

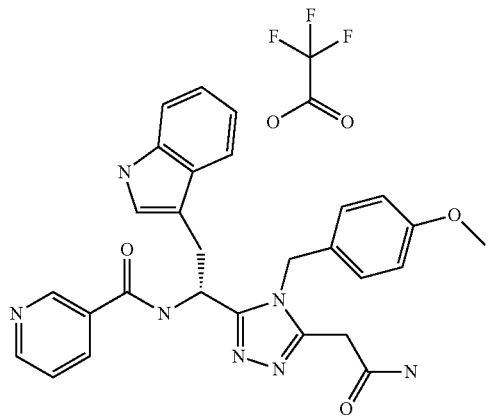

compound 3 Pyridine-2-carboxylic acid [(R)-1-[5-[(R)-1-acetylamino-2-(1H-indol-3-yl)-ethyl]-4-(4-methoxy-benzyl)-4H-[1,2,4]triazol-3-yl]-2-(1H-indol-3-yl)-ethyl]-amide;

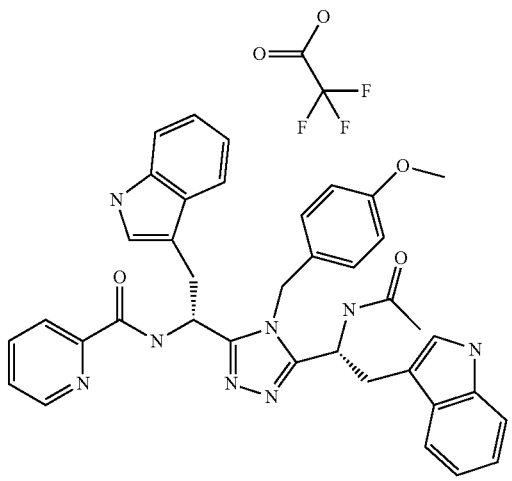

compound 4 Pyridine-2-carboxylic acid [(R)-1-[5-((R)-1-acetylamino-2-phenyl-ethyl)-4-(4-methoxy-benzyl)-4H-[1,2,4]triazol-3-yl]-2-(1H-indol-3-yl)-ethyl]-amide;

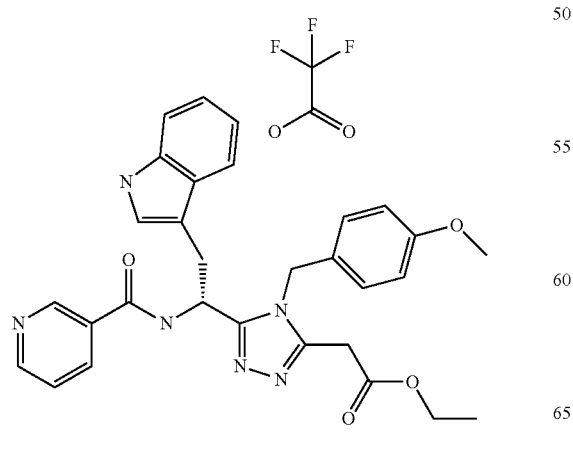

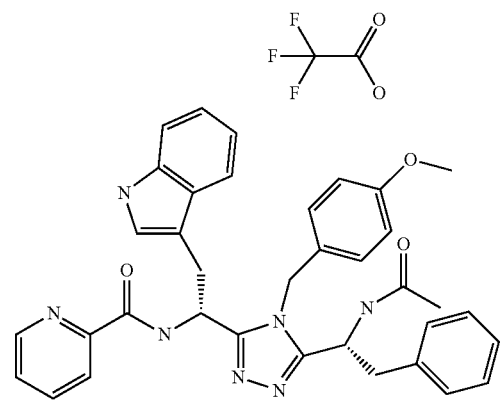 [SMILES: O=C(O)C(F)(F)F ; COc1ccc(Cn2c([C@@H](Cc3ccccc3)NC(C)=O)nnc2[C@@H](Cc2c[nH]c3ccccc23)NC(=O)c2ccccn2)cc1]

compound 5 Pyridine-2-carboxylic acid [(R)-1-[5-((R)-1-formylamino-2-phenyl-ethyl)-4-(4-methoxy-benzyl)-4H-[1,2,4]triazol-3-yl]-2-(1H-indol-3-yl)-ethyl]-amide;

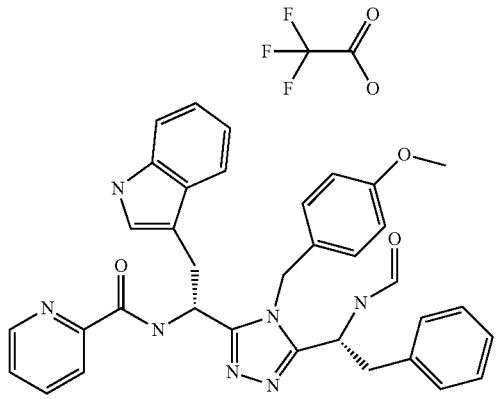 [SMILES: O=C(O)C(F)(F)F ; COc1ccc(Cn2c([C@@H](Cc3ccccc3)NC=O)nnc2[C@@H](Cc2c[nH]c3ccccc23)NC(=O)c2ccccn2)cc1]

compound 6 N-[(R)-1-[5-((R)-1-Acetylamino-2-phenyl-ethyl)-4-(4-methoxy-benzyl)-4H-[1,2,4]triazol-3-yl]-2-(1H-indol-3-yl)-ethyl]-2-hydroxy-acetamide;

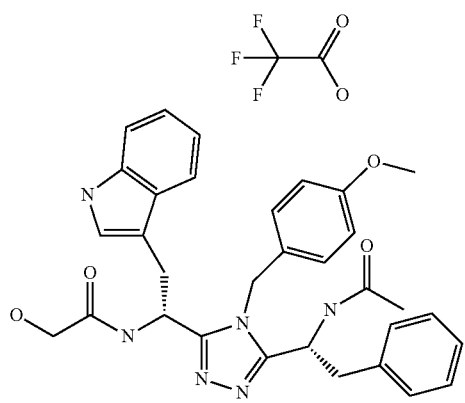 [SMILES: O=C(O)C(F)(F)F ; COc1ccc(Cn2c([C@@H](Cc3ccccc3)NC(C)=O)nnc2[C@@H](Cc2c[nH]c3ccccc23)NC(=O)CO)cc1]

compound 7 (S)-Morpholine-2-carboxylic acid [(R)-1-[5-((R)-1-acetylamino-2-phenyl-ethyl)-4-(4-methoxy-benzyl)-4H-[1,2,4]triazol-3-yl]-2-(1H-indol-3-yl)-ethyl]-amide;

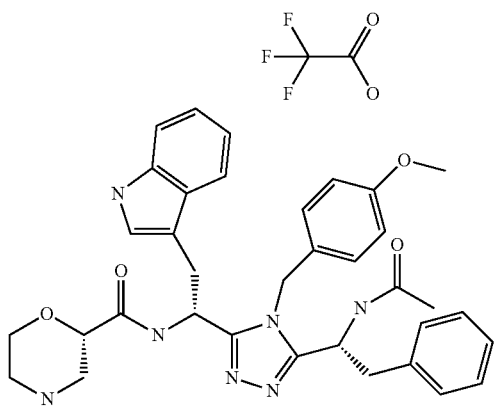 [SMILES: O=C(O)C(F)(F)F ; COc1ccc(Cn2c([C@@H](Cc3ccccc3)NC(C)=O)nnc2[C@@H](Cc2c[nH]c3ccccc23)NC(=O)[C@@H]2CNCCO2)cc1]

compound 8 N-[(R)-1-[5-[(R)-1-Acetylamino-2-(1H-indol-3-yl)-ethyl]-4-(4-methoxy-benzyl)-4H-[1,2,4]triazol-3-yl]-2-(1H-indol-3-yl)-ethyl]-2-amino-2-methyl-propionamide;

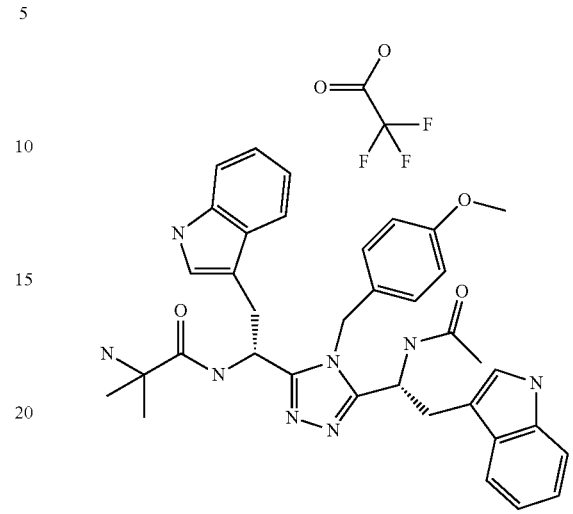

compound 9 2-Amino-N-[(R)-1-[5-[(R)-1-formylamino-2-(1H-indol-3-yl)-ethyl]-4-(4-methoxy-benzyl)-4H-[1,2,4]triazol-3-yl]-2-(1H-indol-3-yl)-ethyl]-2-methyl-propionamide;

compound 10 N-[(R)-1-[5-((R)-1-Acetylamino-2-phenyl-ethyl)-4-(4-methoxy-benzyl)-4H-[1,2,4]triazol-3-yl]-2-(1H-indol-3-yl)-ethyl]-2-amino-2-methyl-propionamide;

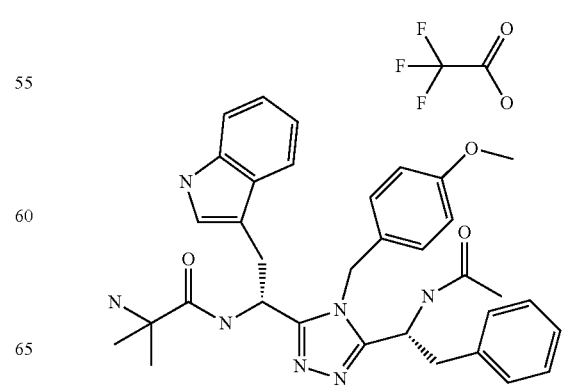

compound 11 Pyridine-2-carboxylic acid [(R)-1-[5-[1-acetylamino-2-(1H-indol-3-yl)-ethyl]-4-(4-methoxy-benzyl)-4H-[1,2,4]triazol-3-yl]-2-(1H-indol-3-yl)-ethyl]-amide;

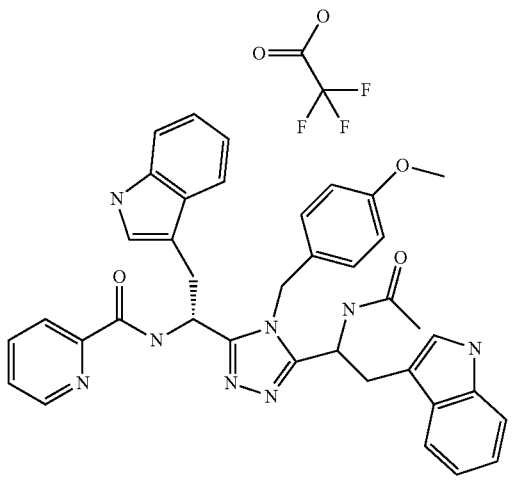

compound 12 2-Amino-N-[(R)-1-[5-((R)-1-formylamino-2-phenyl-ethyl)-4-(4-methoxy-benzyl)-4H-[1,2,4]triazol-3-yl]-2-(1H-indol-3-yl)-ethyl]-2-methyl-propionamide;

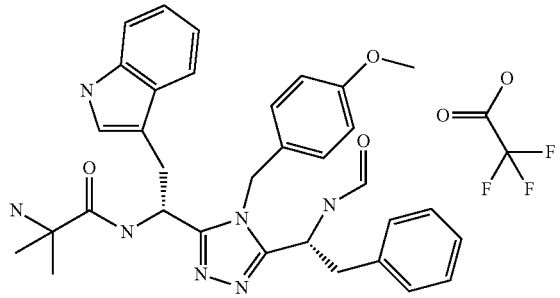

compound 13 Pyridine-2-carboxylic acid [(R)-1-[5-((S)-1-acetylamino-2-phenyl-ethyl)-4-(4-methoxy-benzyl)-4H-[1,2,4]triazol-3-yl]-2-(1H-indol-3-yl)-ethyl]-amide;

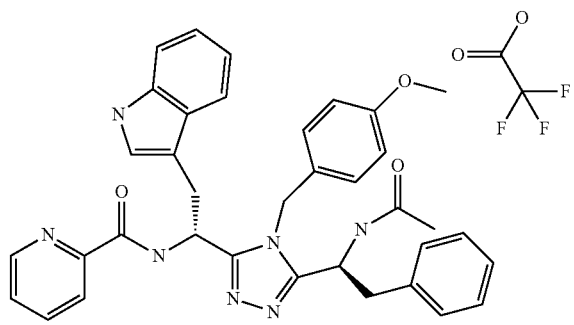

compound 14 Pyridine-2-carboxylic acid [(R)-1-[5-[1-formylamino-2-(1H-indol-3-yl)-ethyl]-4-(4-methoxy-benzyl)-4H-[1,2,4]triazol-3-yl]-2-(1H-indol-3-yl)-ethyl]-amide;

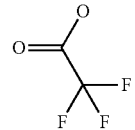
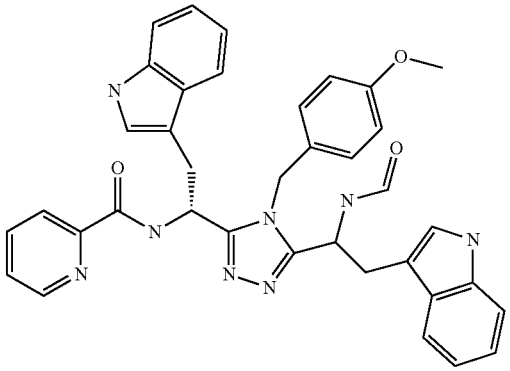

compound 15 {(R)-1-[5-[2-(1H-Indol-3-yl)-ethyl]-4-(4-methoxy-benzyl)-4H-[1,2,4]triazol-3-yl]-2-naphthalen-2-yl-ethyl}-carbamic acid tert-butyl ester;

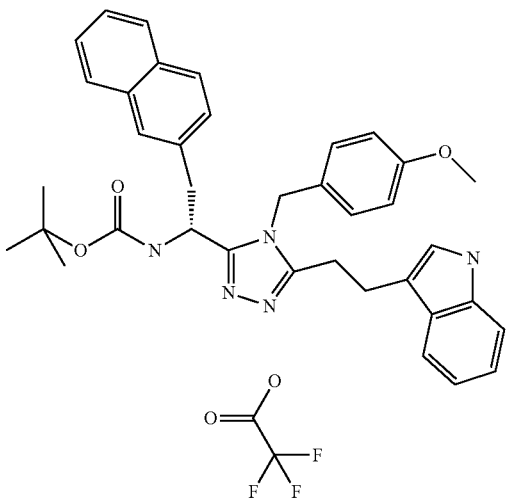 [SMILES: COc1ccc(Cn2c(CCc3c[nH]c4ccccc34)nnc2[C@@H](Cc2ccc3ccccc3c2)NC(=O)OC(C)(C)C)cc1 ; O=C(O)C(F)(F)F]

compound 16 1-{(R)-2-(1H-Indol-3-yl)-1-[4-(4-methoxy-benzyl)-5-phenethyl-4H-[1,2,4]triazol-3-yl]-ethyl}-3-isopropyl-urea;

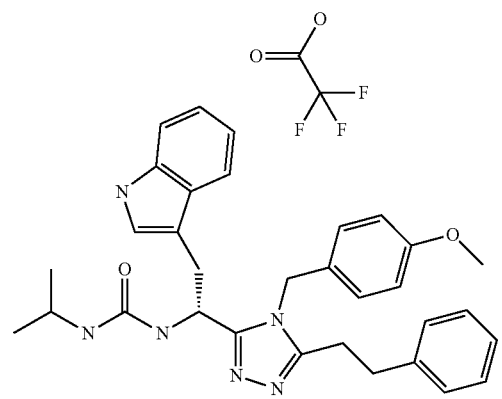 [SMILES: COc1ccc(Cn2c(CCc3ccccc3)nnc2[C@@H](Cc2c[nH]c3ccccc23)NC(=O)NC(C)C)cc1 ; O=C(O)C(F)(F)F]

compound 17 {(R)-2-(1H-Indol-3-yl)-1-[4-(4-methoxy-benzyl)-5-phenethyl-4H-[1,2,4]triazol-3-yl]-ethyl}-carbamic acid isobutyl ester;

compound 20 1-Benzyl-3-{(R)-2-(1H-indol-3-yl)-1-[4-(4-methoxy-benzyl)-5-phenethyl-4H-[1,2,4]triazol-3-yl]-ethyly}-urea;

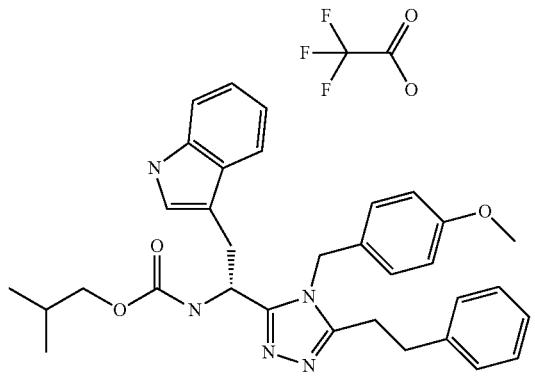 [SMILES: COc1ccc(Cn2c(CCc3ccccc3)nnc2[C@@H](Cc2c[nH]c3ccccc23)NC(=O)OCC(C)C)cc1 ; O=C(O)C(F)(F)F]

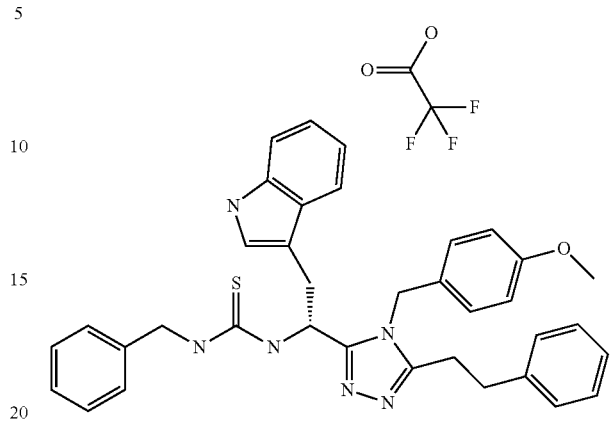

compound 18 {(R)-2-(1H-Indol-3-yl)-1-[4-(4-methoxy-benzyl)-5-phenethyl-4H-[1,2,4]triazol-3-yl]-ethyl}-carbamic acid tert-butyl ester;

compound 21 [(R)-1-[4-(4-Fluoro-benzyl)-5-phenethyl-4H-[1,2,4]triazol-3-yl]-2-(1H-indol-3-yl)-ethyl]-carbamic acid tert-butyl ester;

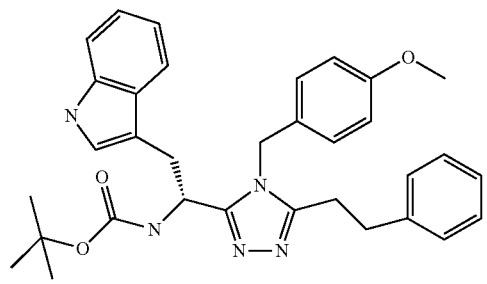

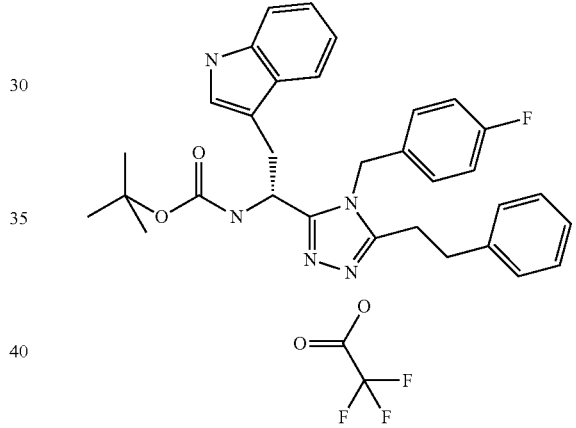

compound 19 1-Benzyl-3-{(R)-2-(1H-indol-3-yl)-1-[4-(4-methoxy-benzyl)-5-phenethyl-4H-[1,2,4]triazol-3-yl]-ethyl}-urea;

compound 22 {(R)-2-(1H-Indol-3-yl)-1-[4-(4-isopropoxy-benzyl)-5-phenethyl-4H-[1,2,4]triazol-3-yl]-ethyl}-carbamic acid tert-butyl ester;

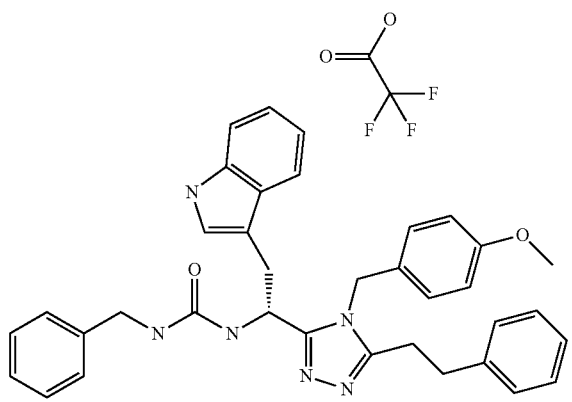 [SMILES: COc1ccc(Cn2c(CCc3ccccc3)nnc2[C@@H](Cc2c[nH]c3ccccc23)NC(=O)NCc2ccccc2)cc1 ; O=C(O)C(F)(F)F]

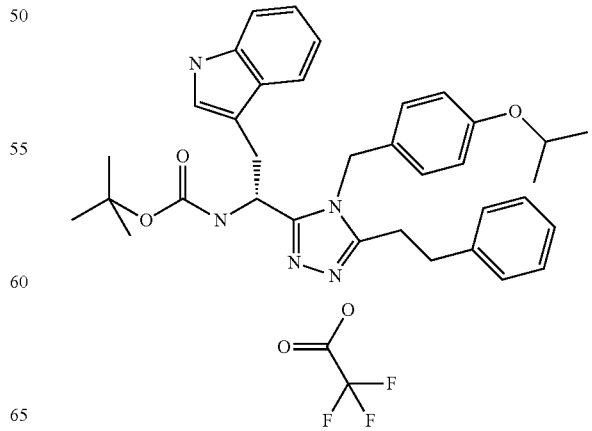

compound 23 {(R)-2-(1H-Indol-3-yl)-1-[4-(4-methoxy-benzyl)-5-phenethyl-4H-[1,2,4]triazol-3-yl]-ethyl}-methyl-carbamic acid tert-butyl ester;

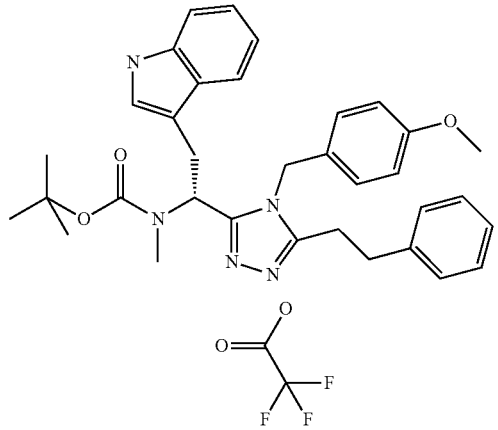

compound 24 [(R)-1-[4-(2,4-Dimethoxy-benzyl)-5-phenethyl-4H-[1,2,4]triazol-3-yl]-2-(1H-indol-3-yl)-ethyl]-carbamic acid tert-butyl ester;

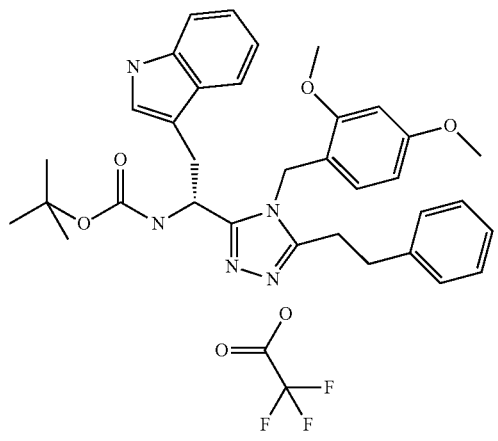

compound 25 Piperidine-4-carbothioic acid {(R)-2-(1H-indol-3-yl)-1-[4-(4-methoxy-benzyl)-5-phenethyl-4H-[1,2,4]triazol-3-yl]-ethyl}-amide;

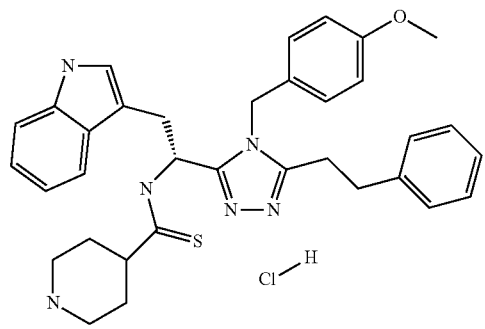 [SMILES: COc1ccc(Cn2c(CCc3ccccc3)nnc2[C@@H](Cc2c[nH]c3ccccc23)NC(=S)C2CCNCC2)cc1 ; Cl]

compound 26 2-Amino-N-{(R)-2-(1H-indol-3-yl)-1-[4-(4-methoxy-benzyl)-5-phenethyl-4H-[1,2,4]triazol-3-yl]-ethyl}-thioacetamide;

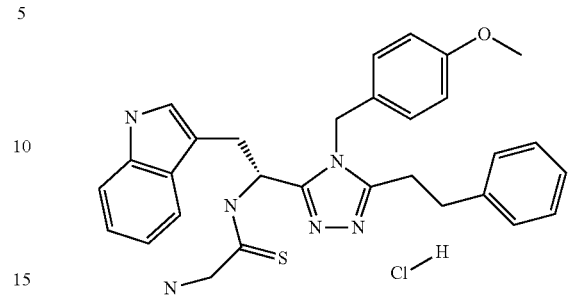

compound 27 Pyridine-2-carbothioic acid {(R)-2-(1H-indol-3-yl)-1-[4-(4-methoxy-benzyl)-5-phenethyl-4H-[1,2,4]triazol-3-yl]-ethyl}-amide;

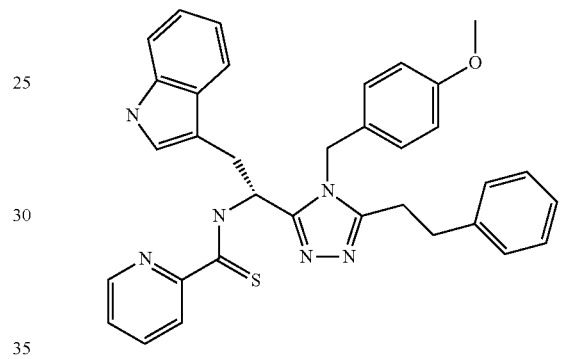

and the physiologically tolerated salts thereof.

The chemical names of the substances were generated using the AutoNom 2000 for ISIS/Draw Add-In.

For the avoidance of doubt, if chemical name and chemical structure of the above illustrated compounds do not correspond by mistake, the chemical structure is regarded to unambiguously define the compound.

In a preferred embodiment these compounds can be used for the manufacture of a medicament for the treatment or prophylaxis of physiological and/or pathophysiological conditions in mammals that are mediated by GHS receptors.

In a further preferred embodiment all triazole compounds as illustrated herein, i.e. generically (by above formula (I) and different R radicals) and explicitly, in the following referred to as the compounds of the (present) invention, can be used for the manufacture of a medicament for the treatment or prophylaxis of physiological and/or pathophysiological conditions in mammals that are mediated by GHS receptors and where the treatment is achieved by modulation of GHS receptors.

The terms indicated for explanation of the above compounds of formula (I) always, unless indicated otherwise in the description or in the claims, have the following meanings:

The term "substituted" means that the corresponding radical or group has one or more substituents. Where a radical has a plurality of substituents, and a selection of various substituents is specified, the substituents are selected independently of one another and need not be identical. The term "unsubstituted" means that the corresponding group has no substituent. The term "optionally substituted" means that the corresponding group is either unsubstituted or substituted by one or more substituents. The term "substituted by up to 3 substituents" means that the corresponding radical or group is substituted either by one or by two or three substituents.

The term "alkyl" includes for the purposes of this invention acyclic saturated hydrocarbons having C1-C12 carbon atoms, which may be straight-chain or branched. The term "alkyl" preferably stands for alkyl chains of 1 to 8, particularly preferably 1 to 6, carbon atoms. Examples of suitable alkyl radicals are methyl, ethyl, n-propyl, isopropyl, n-butyl, isobutyl, sec-butyl, tert-butyl, n-pentyl, tert-pentyl, 2- or 3-methyl-pentyl, n-hexyl, isohexyl, n-heptyl, n-octyl, n-nonyl, n-decyl, n-undecyl, n-dodecyl.

The term "cycloalkyl" stands for a saturated or partially unsaturated non-aromatic cyclic hydrocarbon group/radical, containing 1 to 3 rings, including monocyclic alkyl, bicyclic alkyl and tricyclic alkyl, and containing a total of 3 to 20 carbon atoms forming the rings, preferably 3 to 10, most preferably (C3-C8)-cycloalkyl. Examples of suitable cycloalkyl radicals are cyclopropyl, cyclobutyl, cyclopentyl, cyclohexyl, cycloheptyl, cyclooctyl, cyclodecyl, cyclohexenyl, cyclopentenyl, cyclooctadienyl.

The term "cycloalkylalkyl" refers to a radical in which the cycloalkyl group is linked via an alkyl group, where the alkyl and cycloalkyl groups have the meanings defined herein, preferably a (C3-C8)-cycloalkyl-(C1-C4)-alkyl radical. Examples thereof are cyclopropylmethyl, cyclohexylmethyl, cyclopentylethyl, cyclohexenylethyl.

The term "alkenyl" includes for the purposes of this invention acyclic unsaturated or partially unsaturated hydrocarbons having C2-C12 carbon atoms, which may be straight-chain or branched and contain one or more double bonds. The term "alkenyl" preferably stands for alkenyl chains of 2 to 8, particularly preferably 2 to 6, carbon atoms. Examples are vinyl, propenyl, butenyl, pentenyl, hexenyl, and octadienyl and the like.

The term "alkynyl" refers to acyclic unsaturated or partially unsaturated hydrocarbons having C2-C12 carbon atoms, which may be straight-chain or branched and contain one or more triple bonds. The term "alkynyl" preferably stands for alkynyl chains of 2 to 8, particularly preferably 2 to 6, carbon atoms. Examples are propynyl, butynyl, pentynyl, hexynyl.

The term "aryl" refers to aromatic hydrocarbon systems having 3 to 14, preferably 5 to 14, carbon atoms, which may also be fused to further saturated, (partially) unsaturated or aromatic cyclic systems. Examples of "aryl" are inter alia phenyl, biphenyl, naphthyl and anthracenyl, but also indanyl, indenyl, or 1,2,3,4-tetrahydronaphthyl.

The term "heteroaryl" refers to a 5-, 6- or 7-membered cyclic aromatic radical which comprises at least 1, where appropriate also 2, 3, 4 or 5 heteroatoms, preferably nitrogen, oxygen and/or sulfur, where the heteroatoms are identical or different. The number of nitrogen atoms is preferably between 0 and 3, and that of the oxygen and sulfur atoms is between 0 and 1. The term "heteroaryl" also includes systems in which the aromatic cycle is part of a bi- or polycyclic system, such as were the aromatic cycle is fused to an aryl, cycloalkyl, heteroaryl or heterocyclyl group as defined herein via any desired and possible ring member of the heteroaryl radical. Examples of "heteroaryl" include pyrrolyl, thienyl, furyl, imidazolyl, thiazolyl, isothiazolyl, oxazolyl, isoxazolyl, pyrazolyl, pyridinyl, pyrimidinyl, pyrazinyl, indolyl, quinolinyl, and isoquinolinyl.

The terms "arylalkyl" and "heteroarylalkyl" refer to radicals in which the aryl or heteroaryl radical is linked via an alkyl group, where the alkyl, aryl and heteroaryl groups have the meanings defined herein. Preferred "arylalkyl" groups are phenyl-($C_1$-$C_4$)-alkyl radicals, preferably benzyl or phenylethyl radicals. Preferred "heteroarylalkyl" groups are indolyl-($C_1$-$C_4$)-alkyl radicals, preferably 1H-indole-3-yl-methyl or 2(1H-indole-3-yl)-ethyl.

The term "heterocyclyl" refers to a mono- or polycyclic system of 3 to 14, preferably 5 or 6 to 14 ring atoms which may be exclusively carbon atoms. However, the cyclic system may also comprise 1, 2, 3, 4, or 5 heteroatoms, in particular nitrogen, oxygen and/or sulfur. The cyclic system may be saturated, mono- or polyunsaturated but may not be aromatic. In the case of a cyclic system consisting of at least two rings the rings may be fused or spiro- or otherwise connected. The "heterocyclyl" radical may be attached at any carbon or heteroatom which results in the creation of a stable structure. Examples include pyrrolidinyl, thiapyrrolidinyl, piperidinyl, piperazinyl, oxapiperazinyl, oxapiperidinyl and oxadiazolyl.

The term "heterocyclylalkyl" refers to radicals in which the heterocyclyl group is linked via an alkyl group, where the alkyl and heterocyclyl groups have the meanings defined herein.

The terms "alkylsulfonyl", "arylsulfonyl" and "arylalkyl-sulfonyl" refer to radicals in which the alkyl, aryl or arylalkyl group is linked via a —$SO_2$— group, where the alkyl, aryl and arylalkyl groups have the meanings defined herein. Examples are methylsulfonyl and phenylsulfonyl.

The term "halogen", "halogen atom" or "halogen substituent" (Hal-) refers to one, where appropriate, a plurality of fluorine (F, fluoro), bromine (Br, bromo), chlorine (Cl, chloro), or iodine (I, iodo) atoms. The designations "dihalogen", "trihalogen" and "perhalogen" refer respectively to two, three and four substituents, where each substituent can be selected independently from the group consisting of fluorine, chlorine, bromine and iodine. "Halogen" preferably means a fluorine, chlorine or bromine atom.

The term "natural alpha-amino acid side chain" for the purpose of the present invention refers to all side chains of the known 20 proteinogenic alpha-amino acids as well as to side chains of naturally occurring (i.e. in any biological systems) alpha-amino acids, such as for instance selenocystein, pyrrolysine, citrulline, ornithine, homocysteine, N-methylariginine, N-acetyllysine, gamma-carboxyglutamate, 5-hydroxylysine, 3-methylhistidine and/or N,N,N,-trimethyllysine. In this connection "side chain" refers to the residue that is attached to the alpha-carbon atom, e.g. methyl in case of an Ala side chain or benzyl in case of a Phe side chain.

The term "unnatural alpha amino acid side chain" for the purpose of the present invention refers to all side chains of known alpha-amino acids that are not proteinogenic nor are known to occur naturally (i.e. in any biological systems). Examples are norleucine, cyclohexylglycine, 2-naphthylalanine, substituted alpha-amino acids (e.g. halogen substituted Tyr or Phe) as well as protected alpha-amino acid side chains, where a protection group such as Fmoc, Boc, Z, CBZ, Aloc, trityl, acetyl and/or benzyl is directly attached/reacted to a functionalization (e.g. amino, hydroxy and/or carboxy residue). In this connection "side chain" is referred to as for "natural alpha amino acid side chains".

Above embodiments of radicals R1 to R12 that possess functionalization (e.g. amino, hydroxy and/or carboxy residues), such as alkyl-CO—$NH_2$, -alkyl-CO—OH, -alkyl-$NH_2$, -alkyl-NH—C(NH)—$NH_2$, —CO—C*(R9R10)-$NH_2$, —CO—$CH_2$—C*(R9R10)-$NH_2$, —CO—C*(R9R10)-$CH_2$—$NH_2$ and/or 2-amino-2-carbonyl-propane (2-amino-isobutyric acid/Aib residue), may be protected with protection groups as mentioned above. Such protection group carrying embodiments are regarded as belonging to/within the scope and spirit of the invention.

All stereoisomers of the compounds of the invention are contemplated, either in a mixture or in pure or substantially pure form. The compounds of the present invention can have asymmetric centers at any of the carbon atoms including any one of the R radicals. Consequently, compounds of the invention can exist in the form of their racemates, in the form of the pure enantiomers and/or diastereomers or in the form of mixtures of these enantiomers and/or diastereomers. The mixtures may have any desired mixing ratio of the stereoisomers. All these different stereochemical forms and mixtures are within the scope of the present invention.

Thus, for example, the compounds of the invention which have one or more centers of chirality and which occur as racemates or as diastereomer mixtures can be fractionated by methods known per se into their optical pure isomers, i.e. enantiomers or diastereomers. The separation of the compounds of the invention can take place by column separation on chiral or nonchiral phases or by recrystallization from an optionally optically active solvent or with use of an optically active acid or base or by derivatization with an optically active reagent such as, for example, an optically active alcohol, and subsequent elimination of the radical.

Where possible, the compounds of the invention may be in the form of the tautomers.

It is likewise possible for the compounds of the invention to be in the form of any desired prodrugs such as, for example, esters, carbonates or phosphates, in which cases the actually biologically active form is released only through metabolism. Any compound that can be converted in vivo to provide the bioactive agent (i.e. a compound of the invention) is a prodrug within the scope and spirit of the invention.

Various forms of prodrugs are well known in the art and are described for instance in:
(i) The Practice of Medicinal Chemistry (Wermuth C G et al., Chapter 31, Academic Press 1996);
(ii) Design of Prodrugs (editor: Bundgaard H, Elsevier 1985); and
(iii) A Textbook of Drug Design and Development (Krogsgaard-Larson P and Bundgaard H, eds., Chapter 5: 113-191, Harwood Academic Publishers 1991).

Said references are incorporated herein by reference.

It is further known that chemical substances are converted in the body into metabolites which may where appropriate likewise elicit the desired biological effect—in some circumstances even in more pronounced form.

Any biologically active compound that was converted in vivo by metabolism from any compound of the invention is a metabolite within the scope and spirit of the invention.

The compounds of the invention can, if they have a sufficiently basic group such as, for example, a primary, secondary or tertiary amine, be converted with inorganic and organic acids into salts. The pharmaceutically acceptable salts of the compounds of the invention are preferably formed with hydrochloric acid, hydrobromic acid, iodic acid, sulfuric acid, phosphoric acid, methanesulfonic acid, p-toluenesulfonic acid, carbonic acid, formic acid, acetic acid, sulfoacetic acid, trifluoroacetic acid, oxalic acid, malonic acid, maleic acid, succinic acid, tartaric acid, racemic acid, malic acid, embonic acid, mandelic acid, fumaric acid, lactic acid, citric acid, taurocholic acid, glutaric acid, stearic acid, glutamic acid or aspartic acid. The salts which are formed are, inter alia, hydrochlorides, chlorided, hydrobromides, bromides, iodides, sulfates, phosphates, methanesulfonates, tosylates, carbonates, bicarbonates, formates, acetates, sulfoacetates, triflates, oxalates, malonates, maleates, succinates, tartrates, malates, embonates, mandelates, fumarates, lactates, citrates, glutarate, stearate, aspartates and glutamates. The stoichiometry of the salts formed from the compounds of the invention may moreover be an integral or non-integral multiple of one.

The compounds of the invention can, if they contain a sufficiently acidic group such as, for example, the carboxy, sulfonic acid, phosphoric acid or a phenolic group, be converted with inorganic and organic bases into their physiologically tolerated salts. Examples of suitable inorganic bases are ammonium, sodium hydroxide, potassium hydroxide, calcium hydroxide, and of organic bases are ethanolamine, diethanolamine, triethanolamine, ethylenediamine, t-butylamine, t-octylamine, dehydroabietylamine, cyclohexylamine, dibenzylethylene-diamine and lysine. The stoichiometry of the salts formed from the compounds of the invention can moreover be an integral or non-integral multiple of one.

It is likewise possible for the compounds of the invention to be in the form of their solvates and, in particular, hydrates which can be obtained for example by crystallization from a solvent or from aqueous solution. It is moreover possible for one, two, three or any number of solvate or water molecules to combine with the compounds of the invention to give solvates and hydrates.

It is known that chemical substances form solids which exist in different order states which are referred to as polymorphic forms or modifications. The various modifications of a polymorphic substance may differ greatly in their physical properties. The compounds of the invention can exist in various polymorphic forms, and certain modifications may moreover be metastable. All these polymorphic forms of the compounds of the invention are to be regarded as belonging to the invention.

The triazole derivatives (compounds of the invention) as illustrated herein are ghrelin analogue ligands of GHS receptors. Thus, the aforementioned compounds of the invention are suitable for the treatment or prophylaxis of physiological and/or pathophysiological conditions mediated by GHS receptors and/or physiological and/or pathophysiological conditions which can be influenced by modulation of these receptors, and thus prevented, treated and/or alleviated.

For the purpose of the present invention, the term "treatment" is also intended to include prophylactic treatment or alleviation.

The term "ghrelin analogue ligand" or "ligand" is intended to refer for the purposes of the present invention to every compound which binds in any way to a receptor (the receptors in the present invention being GHS or ghrelin receptors) and induces either activation, inhibition and/or another conceivable effect at this receptor. The term "ghrelin analogue ligand" or "ligand" thus includes agonists, antagonists, partial agonists/antagonists, inverse agonists and other ligands which cause an effect at the receptor which is similar to the effect of agonists, antagonists, partial agonists/antagonists or inverse agonist.

For the purpose of the present invention, the term "GHS or ghrelin receptor antagonist" or "antagonist of GHS or ghrelin receptors" refers to compounds of the invention that bind to GHS or ghrelin receptors but do not elicit a proper activation of the receptors as assessed by recording an increase of intracellular calcium and increase of cAMP response element-driven reporter gene expression, which is characteristic for activation of these G-protein coupled receptors (GPCRs).

The ability to properly inactivate the GHS-R 1A receptors is assessed for any compound of the invention by comparing the degree of inhibition (decrease of intracellular calcium and decrease of cAMP response element-driven reporter gene expression) of GHS-R 1a by the compound to be tested (at varying concentrations in the range of $10^{-10}$ M to $10^{-4}$ M) in the presence of saturating concentrations of ghrelin (0%) compared to the basal level (100%). Such assessment can be readily performed by the skilled artisan due to his expert knowledge. The output is a percentage value for each compound to be tested.

Any compound of the invention that does not show a degree of activation (increase of intracellular calcium and increase of cAMP response element-driven reporter gene expression) of GHS-R 1a of at least 20% as assessed in accordance with above specification is regarded as not eliciting a proper activation and therefore not as GHS or ghrelin receptor agonist. Preferably such compounds do show an antagonizing effect (counteraction/decrease) on ghrelin and/or other GHS stimulated intracellular calcium increase, prevent such stimulation or even act as inverse agonists. An inverse agonists is an ligand which binds to the same receptor binding site as an agonist or antagonist but causes an inhibition of the basal/constitutive activity of the receptor. Such compounds may furthermore exhibit an inhibitory activity on GH secretion and/or on other physiological or pathophysiological conditions or effects, such as food intake or lipogenesis. Their effects may be dissociated. Thus, they may have no impact at all on GH secretion while inhibiting other physiological effects. They may even stimulate other physiological effects.

For the purpose of the present invention, the term "GHS receptor agonist" or "agonist of GHS receptors" refers to compounds of the invention that bind to GHS receptors and elicit a proper activation of the receptor as assessed by recording an increase of intracellular calcium or increase of cAMP response element-driven reporter gene expression, which is characteristic for activation of G-protein coupled receptors.

Any compound of the invention that shows a degree of activation (increase of intracellular calcium and increase of cAMP response element-driven reporter gene expression) of GHS-R 1a of at least 20% as assessed in accordance with above specification is regarded as eliciting a proper activation and therefore as GHS receptor agonist. Such compounds may mimic the effects of ghrelin and/or GHS on GH secretion and for instance food intake or lipogenesis. Like for antagonists, the effects of agonist compounds may be dissociated from the GH secretory effect. Such compounds may even antagonize (counteract/decrease) ghrelin and/or other GHS stimulated intracellular calcium increase.

The term "GHS receptor" or "GHS-R" or "ghrelin receptor" is intended to comprise for the purposes of the present invention receptors that bind at least one known peptidyl and/or non-peptidyl GHS and/or ghrelin. The term "GHS receptor" or "GHS-R" or "ghrelin receptor" is also intended to comprise different GHS binding sites in the various tissues and/or organs as illustrated herein, that bind at least one known peptidyl and/or non-peptidyl GHS and/or ghrelin and which are probably not yet characterized GHS-R subtypes.

Binding of a given known peptidyl and/or non-peptidyl GHS and/or ghrelin can be easily verified by the skilled artisan on the basis of his expert knowledge, e.g. by appropriate binding assays which represent only routine experimentation.

Such GHS receptors may be stimulated/activated by ghrelin (ghrelin responsive) or may not be stimulated/activated by ghrelin (ghrelin non-responsive)—with regard to both acylated and non-acylated ghrelin, respectively. Stimulation/activation of such receptors may cause but does not compulsorily have to elicit GH production and/or GH secretion and/or increase GH plasma levels.

Preferably such GHS receptors are selected from the group consisting of "GHS type 1 receptor, GHS-R 1a, GHS-R 1b, motilin receptor, motilin receptor 1a, neurotensin receptor, TRH receptor, GPR38 (FM1), GPR39 (FM2), FM3, GHS binding site, GHS-R subtype, cardiac GHS-R, mammary GHS-R".

More preferably, such GHS receptors are selected from the group consisting of "GHS type 1 receptor, GHS-R 1a, GHS-R 1b" and most preferably are GHS-R 1a.

As discussed herein, GHS receptors (including GHS binding sites and GHS-R subtypes) are known to be concentrated in the hypothalamus-pituitary area but also appear to be distributed in other central and peripheral tissues. Furthermore, they are also expressed in various tumoral tissues, even in tumoral tissues from organs that do not express these receptors under physiological conditions.

For the purposes of the present invention, all these GHS receptor (including GHS binding sites and GHS-R subtypes) expressing organs and/or tissues are intended to be comprised by the scope of the present invention. Expression of GHS receptors (including GHS binding sites and GHS-R subtypes) in a given organ and/or tissue can be easily verified by the skilled artisan on the basis of his expert knowledge, e.g. by appropriate molecular biologic assays, such as immunofluorescence or immunoprecipitation assays, which represent only routine experimentation.

Preferably, such GHS receptors are located in tissues and/or organs selected from the group consisting of "endocrine tissue, exocrine tissue, peripheral tissue, adipose/fat tissue, brain, hypothalamus, thalamus, hippocampus, striatum, cortex, pituitary, central nervous system, spinal cord, gland, adrenal gland, thyroid gland, salivary gland, mammary gland, neuron, bowel, intestine, stomach, heart, liver, pancreas, kidney, bile, gall, bladder, prostate, spleen, muscle, skeletal muscle, aorta, artery, vein, immune cell, leukocyte, lymphocyte, T cell, B cell, granulocyte, monocyte, macrophage, dendritic cell, mast cell, NK cell, neutrophil, eosinophil, basophil, lymph node, bone, bone marrow, tonsil, thymus, placenta, testes, ovary, uterus, lung, adipocyte, tumor/cancer cell, carcinoma cell, prostate cancer cell, thyroid cancer cell, lung cancer cell, breast cancer cell".

As illustrated supra, the compounds of the invention are ghrelin analogue ligands of GHS receptors. They can be administered to various mammalian species, including human, for the treatment or prophylaxis of physiological and/or pathophysiological condition in such mammals.

For the purpose of the present invention, all mammalian species are regarded as being comprised. Preferably, such mammals are selected from the group consisting of "human, domestic animals, cattle, livestock, pets, cow, sheep, pig, goat, horse, pony, donkey, hinny, mule, hare, rabbit, cat, dog, guinea pig, hamster, rat, mouse". More preferably, such mammals are human.

The compounds of the invention being non-peptidic ghrelin analogue ligands of GHS receptors are surprisingly characterized by a more than threefold improved binding affinity to such receptors for most of them, compared to a representative example, i.e. compound 50 disclosed in WO07/020,013. The compounds of the invention for instance may preferably exhibit an $IC_{50}$ value of less than 100 nM for binding to human GHS-R1a. Most preferably, such compounds may exhibit an $IC_{50}$ value of less than 10 nM for binding to human GHS-R 1a.

Due to their surprisingly strong receptor binding, the compounds of the invention can be advantageously administered at lower doses compared to other less potent binders as disclosed in WO07/020013 while still achieving equivalent or even superior desired biological effects. In addition, such a dose reduction may advantageously lead to less or even no medicinal adverse effects. Further, the high binding specificity of the compounds of the invention may translate into a decrease of undesired side effects on its own regardless of the dose applied.

Furthermore, the compounds of the invention, being of non-peptidic nature, are resistant to degradation by enzymes of the gastro-intestinal tract. Hence, they offer the advantage to be given by oral route. They surprisingly display an improved metabolic stability and/or an improved bioavailability. Hence, again an advantageous dose reduction may be achievable which may cause less or even no side effects.

The compounds of the invention can be agonists, antagonists or partial agonists/antagonists or inverse agonists of GHS or ghrelin receptors as illustrated and defined herein.

The compounds of the invention can either be antagonists or agonists of GHS receptors as illustrated and defined herein.

GHS receptor antagonists of the present invention can for instance be employed for the inhibition of GHS receptors stimulated by ghrelin and/or other GHS thus decreasing and/or blocking GH production and/or secretion and/or GH plasma levels. In addition, such GHS receptor antagonists may also be employed for the inhibition or prevention of physiological or pathophysiological effects of ghrelin which are not related to GH production and/or GH secretion.

Therefore, GHS receptor antagonists of the present invention are suitable for the treatment and/or prophylaxis of various physiological and pathophysiological conditions as disclosed herein, in particular for the short-, medium- and/or long term regulation of energy balance, the short-, medium- and/or long term regulation (stimulation and/or inhibition) of food intake, the treatment of adipogenesis, adiposity and/or obesity, body weight gain and/or reduction and the treatment of tumor cell proliferation.

In contrast, GHS receptor agonists of the present invention can for instance be employed for the activation of GHS receptors and stimulation/increase of GH production and/or GH secretion and would thus have similar effects or uses as growth hormone itself, ghrelin and/or known GHS.

Thus, GHS receptor agonists of the present invention are suitable for the treatment and/or prophylaxis of various physiological and pathophysiological conditions as disclosed herein, in particular for growth retardation, cachexia, inflammation, inflammatory effects, gastric postoperative ileus, postoperative ileus and/or gastrectomy (ghrelin replacement therapy).

For the purpose of the present invention, all physiological and/or pathophysiological conditions are intended to be comprised that are known to be mediated by GHS receptors.

Preferably, these physiological and/or pathophysiological conditions are selected from the group consisting of "acute fatigue syndrome and muscle loss following election surgery, adipogenesis, adiposity, age-related decline of thymic function, age-related functional decline ("ARFD") in the elderly, aging disorder in companion animals, alcohol-related disorders, Alzheimer's disease, anorexia (e.g. associated with cachexia or aging); anxiety, blood pressure (lowering), body weight gain/reduction, bone fracture repair (acceleration), bone remodeling stimulation, cachexia and protein loss reduction due to chronic illness such as cancer or AIDS, cardiac dysfunctions (e.g. associated with valvular disease, myocardial infarction, cardiac hypertrophy or congestive heart failure), cardiomyopathy, cartilage growth stimulation, catabolic disorders in connection with pulmonary dysfunction and ventilator dependency, catabolic side effects of glucocorticoids, catabolic state of aging, central nervous system disorders (in combination with antidepressants), chronic dialysis, chronic fatigue syndrome (CFS), cognitive function improvement (e.g. in dementia, Alzheimer's disease), complicated fractures (e.g. disctraction osteogenesis), complications associated with transplantation, congestive heart failure (alone/in combination with corticotropin releasing factor antagonists), Crohn's disease and ulcerative colits, Cushing's syndrome, dementia, depressions, drug abuse, short-, medium- and/or long-term regulation of energy balance, short-, medium- and/or long-term regulation of food intake (stimulation and/or inhibition), intake of rewarding food, fraility (e.g. in elderly humans), gastrectomy (ghrelin replacement therapy), gastric postoperative ileus, glycemic control improvement, growth hormone release stimulation in the elderly, growth hormone replacement in stressed patients, growth promotion in livestock, growth retardation associated with the Prader-Willi syndrome and Turner's syndrome, growth retardation in connection with Crohn's disease, growth retardation, hair/nail growth maintenance, hip fractures, hunger, hypercortisolism, hyperinsulinemia including nesidioblastosis, hypothermia, immune deficiency in individuals with a depressed T4/T8 cell ratio, immune response improvement to vaccination, immune system stimulation in companion animals, immune system stimulation, immunosuppression in immunosuppressed patients, inflammation or inflammatory effects, inflammatory bowel disease, insulin resistance in the heart, insulin resistance in type 2 diabetic patients, insulin resistance including NIDDM, diabetes, diabetes type I, diabetes type II, intrauterine growth retardation, irritable bowel syndrome, lipodystrophy (e.g. HIV-induced), metabolic homeostasis maintenance, milk production increase in livestock, muscle mass/strength increase, muscle mobility improvement, muscle strength improvement, muscle strength/function maintenance in elderly humans, muscular atrophy, musculoskeletal impairment (e.g. in elderly), Noonan's syndrome, obesity and growth retardation associated with obesity, osteoblast stimulation, osteochondrodysplasias, osteoporosis, ovulation induction (adjuvant treatment), physiological short stature including growth hormone deficient children, postoperative ileus, protein catabolic response attenuation after major surgery/trauma, protein kinase B activity enhancement, psychosocial deprivation, pulmonary dysfunction and ventilator dependency, pulmonary function improvement, pulsatile growth hormone release induction, recovery of burn patients and reducing hospitalization of burn patients (acceleration), renal failure or insufficiency resulting from growth retardation, renal homeostasis maintenance in the frail elderly, sarcopenia, schizophrenia, sensory function maintenance (e.g. hearing, sight, olefaction and taste), short bowel syndrome, short stature associated with chronic illness, skeletal dysplasia, skin thickness maintenance, sleep disorders, sleep quality improvement, thrombocytopenia, thymic development stimulation, tooth repair or growth, tumor cell proliferation, ventricular dysfunction or reperfusion events, wasting in connection with AIDS, wasting in connection with chronic liver disease, wasting in connection with chronic obstructive pulmonary disease (COPD), wasting in connection with multiple sclerosis or other neurodegenerative disorders, wasting secondary to fractures, wool growth stimulation in sheep, wound healing (acceleration), wound healing delay".

More preferably these physiological and/or pathophysiological conditions are selected from the group consisting of "alcohol-related disorders; drug abuse; growth retardation, cachexia, short-, medium- and/or long term regulation of energy balance; short-, medium- and/or long term regulation (stimulation and/or inhibition) of food intake; intake of rewarding food; adipogenesis, adiposity and/or obesity; body weight gain and/or reduction; diabetes, diabetes type I, diabetes type II, tumor cell proliferation; inflammation, inflammatory effects, gastric postoperative ileus, postoperative ileus and/or gastrectomy (ghrelin replacement therapy)".

More recent findings indicate that the effects of ghrelin on food intake are partly mediated by the mesolimbic dopamine systems involved in reward-seeking behaviour (Jerlhag E. et al. 2006 Addiction Biology 11:45-54; Jerlhag E, et al. Addict Biol. 2007 12:6-16; Egecioglu E. et al. 2010, Addiction Biology 15, 304-311). In addition, most recent data confirm the suitability of ghrelin antagonists for the treatment of alcohol-related disorders (WO2009/020419 and Jerlhag et al. 2009. PNAS 106, 11318-11323) and drug abuse (Jerlhag E. et al. 2010, Psychopharmacology 211, 415-422).

In a further aspect of the present invention, the compounds of the invention may be used in combination with at least one additional pharmacologically active substance.

Such additional pharmacologically active substance may be other compounds of the present invention and/or other "suitable therapeutic agents" useful in the treatment and/or prophylaxis of the aforementioned physiological and/or pathophysiological conditions. The additional pharmacologically active substance may be an antagonist of GHS receptors and/or an agonist of GHS receptors depending on the purpose of the combined use. Selection and combination of the additional pharmacologically active substance(s) can be easily performed by the skilled artisan on the basis of his expert knowledge and depending on the purpose of the combined use and physiological and/or pathophysiological conditions targeted.

In a preferred embodiment, the compounds of the invention are used for the treatment and/or prophylaxis of the aforementioned physiological and/or pathophysiological conditions in the form of a medicament, where such medicament comprises at least one additional pharmacologically active substance.

In another preferred embodiment, the compounds of the invention are used for the treatment and/or prophylaxis of the aforementioned physiological and/or pathophysiological conditions in the form of a medicament, where the medicament is applied before and/or during and/or after treatment with at least one additional pharmacologically active substance.

The above mentioned "suitable therapeutic agents" include: "GHS, anti-diabetic agents; anti-osteoporosous agents; anti-obesity agents; anti-inflammatory agents; anti-anxiety agents; anti-depressants; anti-hypertensive agents; anti-platelet agents; antithrombotic and thrombolytic agents; cardiac glycosides; cholesterol/lipid lowering agents; mineralocorticoid receptor antagonists; phosphodiesterase inhibitors; protein tyrosine kinase inhibitors; thyroid mimetics (including thyroid receptor antagonists); anabolic agents; HIV or AIDS therapies; therapies useful in the treatment of Alzheimer's disease and other cognitive disorders; therapies useful in the treatment of sleeping disorders; anti-proliferative agents; anti-tumor agents; anti-ulcer and gastroesopheageal reflux disease agents; progestin receptor agonists ("PRA"); estrogen; testosterone; a selective estrogen receptor modulator; a selective androgen receptor modulator; parathyroid hormone; and/or bisphosphonate", and preferably, a "suitable therapeutic agents" is selected of the group consisting of this agents.

Examples of suitable GHS for use in combination with the compounds of the present invention include GHRP-6, GHRP-1 as described in U.S. Pat. No. 4,411,890; and publications WO 89/07110 and WO 89/07111 and B-HT920 or growth hormone releasing factor and its analogs or growth hormone and its analogs or somatomedins including IGF-1 and IGF-2 as well as GHS described in WO 01/96300.

Examples of suitable anti-diabetic agents for use in combination with the compounds of the present invention include biguanides (e.g. metformin), glucosidase inhibitors (e.g. acarbose), insulins (including insulin secretagogues or insulin sensitizers), meglitinides (e.g. repaglinide), sulfonylureas (e.g., glimepiride, glyburide and glipizide), biguanide/glyburide combinations (e.g., glucovance), thiozolidinediones (e.g. troglitazone, rosiglitazone and pioglitazone), PPAR-alpha agonists, PPAR-gamma agonists, PPAR alpha/gamma dual agonists, SGLT2 inhibitors, inhibitors of fatty acid binding protein (aP2) such as those disclosed in U.S. Pat. No. 6,548,529, glucagon-like peptide-1 (GLP-1), and dipeptidyl peptidase IV (DP4) inhibitors.

Examples of suitable anti-osteoporosous agents for use in combination with the compounds of the present invention include alendronate, risedronate, raloxifene, calcitonin, nonsteroidal progestin receptor agonists, RANK ligand agonists, calcium sensing receptor antagonists, TRAP inhibitors, selective estrogen receptor modulators (SERM), estrogen and AP-1 inhibitors.

Examples of suitable anti-obesity agents for use in combination with the compounds of the present invention include endocannabinoid receptor antagonists, e.g. CB1 receptor antagonists such as rimonabant (1H-Pyrazole-3-carboxamide, 5-(4-chlorophenyl)-1-(2,4-dichlorophenyl)-4-methyl-N-1-piperidinyl-, monohydrochloride; CAS Registry Number: 158681-13-1; SR-141716A; U.S. Pat. No. 5,624,941), aP2 inhibitors such as those disclosed in U.S. Pat. No. 6,548,529, PPAR gamma antagonists, PPAR delta agonists, and orlistat.

Examples of suitable antinflammatory agents for use in combination with the compounds of the present invention include prednisone, dexamethasone, Enbrel, cyclooxygenase inhibitors (i.e., COX-1 and/or COX-2 inhibitors such as NSAIDs, aspirin, indomethacin, ibuprofen, piroxicam, Naproxen, Celebrex, Vioxx), CTLA4-Ig agonists/antagonists, CD40 ligand antagonists, integrin antagonists, alpha4 beta7 integrin antagonists, cell adhesion inhibitors, interferon gamma antagonists, ICAM-1, tumor necrosis factor (TNF) antagonists (e.g., infliximab, OR1384), prostaglandin synthesis inhibitors, budesonide, clofazimine, CNI-1493, CD4 antagonists (e.g., priliximab), p38 mitogen-activated protein kinase inhibitors, protein tyrosine kinase (PTK) inhibitors, IKK inhibitors, and therapies for the treatment of irritable bowel syndrome (e.g., zelmac and Maxi-K openers such as those disclosed in U.S. Pat. No. 6,184,231).

Examples of suitable anti-anxiety agents for use in combination with the compounds of the present invention include diazepam, lorazepam, buspirone, oxazepam, and hydroxyzine pamoate.

Examples of suitable anti-depressants for use in combination with the compounds of the present invention include citalopram, fluoxetine, nefazodone, sertraline, and paroxetine.

Examples of suitable anti-hypertensive agents for use in combination with the compounds of the present invention include beta adrenergic blockers, calcium channel blockers (L-type and T-type; e.g. diltiazem, verapamil, nifedipine, amlodipine and mybefradii), diruetics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan and compounds disclosed in U.S. Pat. Nos. 5,612,359 and 6,043,265, Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates.

Examples of suitable anti-platelet agents for use in combination with the compounds of the present invention include GPIIb/IIIa blockers (e.g., abciximab, eptifibatide, tirofiban), P2Y12 antagonists (e.g., clopidogrel, ticlopidine, CS-747), thromboxane receptor antagonists (e.g., ifetroban), aspirin, and PDE-III inhibitors (e.g., dipyridamole) with or without aspirin.

Examples of suitable cardiac glycosides for use in combination with the compounds of the present invention include digitalis and ouabain.

Examples of suitable cholesterol/lipid lowering agents for use in combination with the compounds of the present invention include HMG-CoA reductase inhibitors [e.g., pravastatin lovastatin, atorvastatin, simvastatin, NK-104 (a.k.a. itavastatin, or nisvastatin or nisbastatin] and ZD-4522 (a.k.a. rosuvastatin, or atavastatin or visastatin)), squalene synthetase inhibitors, fibrates, bile acid sequestrants, ACAT inhibitors, MTP inhibitors, lipooxygenase inhibitors, choesterol absorption inhibitors, and cholesterol ester transfer protein inhibitors (e.g., CP-529414).

Examples of suitable mineralocorticoid receptor antagonists for use in combination with the compounds of the present invention include spironolactone and eplerinone.

Examples of suitable phosphodiesterase inhibitors for use in combination with the compounds of the present invention include PDE III inhibitors such as cilostazol, and PDE V inhibitors such as sildenafil.

Examples of suitable thyroid mimetics for use in combination with the compounds of the present invention include thyrotropin, polythyroid, KB-130015, and dronedarone.

Examples of suitable anabolic agents for use in combination with the compounds of the present invention include testosterone and SARMs.

Examples of suitable HIV or AIDS therapies for use in combination with the compounds of the present invention include indinavir sulfate, saquinavir, saquinavir mesylate, amprenavir, ritonavir, lopinavir, ritonavir/lopinavir combinations, lamivudine, zidovudine, lamivudine/zidovudine combinations, zalcitabine, didanosine, stavudine, and megestrol acetate.

Examples of suitable therapies for treatment of Alzheimer's disease and cognitive disorders for use in combination with the compounds of the present invention include donepezil, tacrine, revastigmine, 5HT6, gamma secretase inhibitors, beta secretase inhibitors, SK channel blockers, Maxi-K blockers, and KCNQs blockers.

Examples of suitable therapies for treatment of sleeping disorders for use in combination with the compounds of the present invention include melatonin analogs, melatonin receptor antagonists, ML1B agonists, and GABA/NMDA receptor antagonists.

Examples of suitable anti-proliferative agents for use in combination with the compounds of the present invention include cyclosporin A, taxol, FK 506, and adriamycin.

Examples of suitable anti-tumor agents for use in combination with the compounds of the present invention include taxol, adriamycin, epothilones, cisplatin and carboplatin.

Examples of suitable a selective estrogen receptor modulator for use in combination with the compounds of the present invention include tamoxifen and raloxifene.

Examples of suitable a selective androgen receptor modulator for use in combination with the compounds of the present invention include such disclosed in Edwards, J. P. et al., Bio. Med. Chem. Let., 9, 1003-1008 (1999) and Hamann, L. G. et al., J. Med. Chem., 12, 210-212 (1999).

Examples of suitable a bisphosphonate for use in combination with the compounds of the present invention include MK-217 (alendronate).

The above other therapeutic agents, when employed in combination with the compounds of the present invention, may be used, for example, in those amounts indicated in the Physicians' Desk Reference (PDR) or as otherwise determined by one of ordinary skill in the art.

In a preferred embodiment, the compounds of the invention are used for the treatment and/or prophylaxis of the aforementioned physiological and/or pathophysiological conditions in the form of a medicament, where such medicament comprises as additional pharmacologically active substance an endocannabinoid receptor antagonist, preferably a CB1 receptor antagonist, most preferably rimonabant (1H-Pyrazole-3-carboxamide, 5-(4-chlorophenyl)-1-(2,4-dichlorophenyl)-4-methyl-N-1-piperidinyl-, monohydrochloride; CAS Registry Number: 158681-13-1; SR-141716A; U.S. Pat. No. 5,624,941) and as compound of the invention a GHS-R antagonist.

In another preferred embodiment, the compounds of the invention are used for the treatment and/or prophylaxis of the aforementioned physiological and/or pathophysiological conditions in the form of a medicament, where the medicament is applied before and/or during and/or after treatment with at least one additional pharmacologically active substance, where such additional pharmacologically active substance is an endocannabinoid receptor antagonist, preferably a CB1 receptor antagonist, most preferably rimonabant (1H-Pyrazole-3-carboxamide, 5-(4-chlorophenyl)-1-(2,4-dichlorophenyl)-4-methyl-N-1-piperidinyl-, monohydrochloride; CAS Registry Number: 158681-13-1; SR-141716A; U.S. Pat. No. 5,624,941) and the compound of the invention is a GHS-R antagonist.

The compounds of the present invention can be administered in a known manner. The route of administration may thereby be any route which effectively transports the active compound to the appropriate or desired site of action, for example orally or non-orally, in particular topically, transdermally, pulmonary, rectally, intravaginally, nasally or parenteral or by implantation. Oral administration is preferred.

The compounds of the invention are converted into a form which can be administered and are mixed where appropriate with pharmaceutically acceptable carriers or diluents. Suitable excipients and carriers are described for example in Ullman's Encyclopedia of Technical Chemistry, Vol. 4, (1953), 1-39; Journal of Pharmaceutical Sciences, Vol. 52 (1963), 918 et seq.; H. v. Czetsch-Lindenwald, "Hilfsstoffe für Pharmazie and angrenzende Gebiete"; Pharm. Ind. 2, 1961, 72 et seq.; Dr. H. P. Fiedler, "Lexikon der Hilfsstoffe für Pharmazie, Kosmetik and angrenzende Gebiete", Cantor K G, Aulendorf in Württemberg, 1971.

Oral administration can take place for example in solid form as tablet, capsule, gel capsule, coated tablet, granulation or powder, but also in the form of a drinkable solution. The compounds of the invention can for oral administration be combined with known and ordinarily used, physiologically tolerated excipients and carriers such as, for example, gum arabic, talc, starch, sugars such as, for example, mannitol, methylcellulose, lactose, gelatin, surface-active agents, magnesium stearate, cyclodextrins, aqueous or nonaqueous carriers, diluents, dispersants, emulsifiers, lubricants, preservatives and flavorings (e.g. essential oils). The compounds of the invention can also be dispersed in a microparticulate, e.g. nanoparticulate, composition.

Non-oral administration can take place for example by intravenous, subcutaneous, intramuscular injection of sterile aqueous or oily solutions, suspensions or emulsions, by means of implants or by ointments, creams or suppositories. Administration as sustained release form is also possible where appropriate. Implants may comprise inert materials, e.g. biodegradable polymers or synthetic silicones such as, for example, silicone rubber. Intravaginal administration is possible for example by means of vaginal rings. Intrauterine administration is possible for example by means of diaphragms or other suitable intrauterine devices. Transdermal administration is additionally provided, in particular by means of a formulation suitable for this purpose and/or suitable means such as, for example, patches.

The dosage may vary within a wide range depending on type and/or severity of the physiological and/or pathophysiological condition, the mode of administration, the age, gender, bodyweight and sensitivity of the subject to be treated. It is within the ability of a skilled worker to determine a "pharmacologically effective amount" of a compound of the invention and/or additional pharmacologically active substance. Administration can take place in a single dose or a plurality of separate dosages.

A suitable unit dose is, for example, from 0.001 mg to 100 mg of the active ingredient, i.e. at least one compound of the invention and, where appropriate, at least one additional pharmacologically active substance, per kg of a patient's bodyweight.

In another aspect, the present invention relates to a pharmaceutical composition comprising a pharmacologically active amount of at least one triazole compound selected from the group consisting of: compound 1, 2, 3, 4, 5, 6, 7, 8, 9, 10, 11, 12, 13, 14, 15, 16, 17, 18, 19, 20, 21, 22, 23, 24, 25, 26 and/or 27, In a further aspect, such a pharmaceutical composition may additionally comprise at least one pharmaceutically acceptable carrier and/or excipient and/or may comprise at least one further pharmacologically active substance.

In a preferred embodiment, such further pharmacologically active substance is an endocannabinoid receptor antagonist, preferably a CB1 receptor antagonist, most preferably rimonabant [1H-Pyrazole-3-carboxamide, 5-(4-chlorophenyl)-1-(2,4-dichlorophenyl)-4-methyl-N-1-piperidinyl-, monohydrochloride].

Concerning the pharmaceutical compositions of the invention, at least one of the triazole compounds as listed above is present in a pharmacologically effective amount, preferably in a unit dose, e.g. the aforementioned unit dose, specifically and preferably in an administration form which makes oral administration possible. Furthermore, reference may be made to that already said in connection with the possible uses and administrations of the compounds of the invention.

GHS-R 1a Receptor Assays

Mouse LTK-cells (ATCC CCL-1.3) were stably transfected with a plasmid containing the CMV minimal promoter (CMVmin) linked to three cAMP response elements (CRE) followed by a luciferase reporter gene. Based on this parental cell line, single cell clones stably overexpressing the human, rat or mouse GHS-R 1A have been established and characterized with respect to suitability for the different assay formats.

For receptor competitive binding studies, iodinated ghrelin was used as a tracer at conditions of about 80% saturation binding. Different concentrations of the test compounds were analyzed for displacement of the tracer. For this purpose, the suspension of intact cells plus tracer mix and different test compound concentrations was layered on top of silicon/paraffin oil, incubated for 60 min at 37° C. and subjected to centrifugation. After freezing in liquid nitrogen the cell pellets were separated from the supernatant by cutting the tubes in the intermediate silicon/paraffin oil section and analyzed by γ-radiation analysis. The amount of unspecific binding was determined by including unlabeled ghrelin at 1 µM final concentration.

For the CRE/Luc reporter gene assay, the mouse LTK-cells stably expressing the human GHS-1RA and a luciferase reporter gene under the control of CRE elements and the CMV minimal promoter were incubated for 6 h with 1 µM rolipram in the presence of different concentrations of AEZS-130. Subsequently, cells were lysed and ATP bioluminescence was measured in the luminescence mode on FlexStation3 (Molecular Devices).

For determination of calcium release the respective cell line was loaded with Fluo-4 NW Calcium Assay Kit (Moleculare Probes/Invitrogen # F10741) for 80 min @ 37° C. After 15 minutes of preincubation with different concentrations of the test compounds ghrelin was added and the signal was monitored for 60 seconds by a FlexStation3 microplate reader (Molecular Devices).

All data were calculated in % inhibition according to cells treated with saturating concentrations of ghrelin (NeoMPS #sc1357) as negative (0% inhibition), and non-treated cells as positive control (100%). $IC_{50}$ values were determined by using the GraphPad Prism analysis program (GraphPad Software).

In the following table 1 results obtained for selected compounds of the invention are presented in comparison to compound 50 disclosed in WO07/020,013. Values given are either single measurements or mean values of up to nine independent experiments performed in duplicate (binding) or quadruplicate (functional assays) measurements.

TABLE 1

Shown in table 1A and 1B on the next two pages are mean IC$_{50}$ values for ghrelin antagonistic activity of selected compounds against ghrelin receptors of men, rats and mice.

| | | Inhibition of the Ghrelin Receptor | | | | |
|---|---|---|---|---|---|---|
| | | Human Ghrelin Receptor Antagonist | | | Rat Ghrelin Receptor | Mouse Ghrelin Receptor |
| Compound | MW | Competitive Binding IC50 [µM] | CRE/Luc Reporter Gene Assay IC50 [µM] | Calcium Release IC50 [µM] | Antagonist Calcium Release IC50 [µM] | Antagonist Calcium Release IC50 [µM] |
| Table 1A | | | | | | |
| Cpd 50 WO07/020013 | 545 | 0.0163 | 0.1334 | 0.0629 | 3.831 | 2.496 |
| Cpd 3 | 767 | 0.0006 | 0.0022 | 0.0025 | 0.0299 | 0.0292 |
| Cpd 4 | 728 | 0.0013 | 0.0043 | 0.0020 | 0.2390 | 0.0687 |
| Cpd 6 | 681 | 0.0030 | 0.0078 | 0.0021 | | |
| Cpd 5 | 714 | 0.0034 | 0.0083 | 0.0031 | 0.2901 | 0.0893 |
| Cpd 7 | 736 | 0.0034 | 0.0095 | 0.0038 | | |
| Table 1B | | | | | | |
| Cpd 50 WO07/020013 | 545 | 0.0163 | 0.1334 | 0.0629 | 3.831 | 2.496 |
| Cpd 1 | 653 | | 0.0128 | 0.0030 | | |
| Cpd 17 | 666 | 0.0086 | 0.0211 | 0.0314 | 0.9248 | 0.6065 |
| Cpd 8 | 747 | 0.0014 | 0.0224 | 0.0191 | 1.053 | 0.3632 |
| Cpd 15 | 716 | 0.0165 | 0.0249 | 0.0399 | | |
| Cpd 9 | 733 | 0.0032 | 0.0586 | 0.0326 | | |

Ghrelin receptor IC$_{50}$ values shown in bold letters are at least three fold improved compared to the respective IC$_{50}$ value obtained for compound 50 disclosed in WO07/020013.

In Vitro Safety Assessment

For detection of MDR-1 (P-glycoprotein, Pgp) ATPase activity commercially available membrane preparations of MDR-1 overexpressing SF9 insect cells (SB-MDR1-Sf9-ATPase Membrane; 2.5 mg/500 µL; Solvo/tebu-bio #168SB-MDR1-Sf9-ATPase) were used. Since transport by MDR-1 is ATP-dependent, ATP consumption indicates transport activity of MDR-1. ATP consumption is detected as a decrease in luminescence from a second reaction with a recombinant firefly luciferase by using the Pgp-Glo™ Assay Kit (Promega # V3591).

The Predictor™ hERG Fluorescence Polarization Assay (Invitrogen, Karlsruhe, GER) determines whether test compounds block the hERG channel [Piper, D. R. et al., Assay Drug Dev Technol. 2008, 6(2):213-23]. The assay uses a membrane fraction containing hERG channel protein (Predictor™ hERG Membrane) and a high-affinity red fluorescent hERG channel ligand, or "tracer" (Predictor™ hERG Tracer Red), in a homogenous, fluorescence polarization (FP)-based format. Compounds that bind to the hERG channel protein (competitors) are identified by their ability to displace the tracer, resulting in a lower fluorescence polarization. The assay was performed according to guidelines of the manufacturer Direct and metabolism-dependent inhibition of CYP enzymes are assessed with specific marker substrates by a HPLC-based UV detection method in human liver microsomes. Incubations are carried out as doublets with final concentrations ranging from 0.01 to 200 µM (30 min, 37° C.). Metabolism-dependent inhibition was assessed by incubation for 30 minutes in the presence of NADPH prior to the addition of marker substrate to allow the generation of metabolites. Percent inhibition is plotted against concentration to calculate or extrapolate IC$_{50}$ values from the sigmoid curve.

TABLE 2

Shown in table 2A and 2B on the next two pages are the EC$_{50}$ results of in vitro safety parameter, i.e. inhibition of the human transporter MDR-1 (Pgp), the hERG cardiac channel, and the CYP3A4 enzyme.

| | In vitro Safety Assessment | | | | | |
|---|---|---|---|---|---|---|
| Compound | Inhibition of MDR1 ATPase EC50 [µM] | hERG Predictor EC50 [µM] | CYP3A4 Inhibition Testosteron EC50 [µM] | CYP3A4 Inhibition Testosteron Preincubation EC50 [µM] | CYP3A4 Inhibition Midazolam EC50 [µM] | CYP3A4 Inhibition Midazolam Preincubation EC50 [µM] |
| Table 2A | | | | | | |
| Cpd 50 WO07/020013 | 6.95 | 8.17 | 6.3 | | 7.3 | 3 |

TABLE 2-continued

Shown in table 2A and 2B on the next two pages are the $EC_{50}$ results of in vitro safety parameter, i.e. inhibition of the human transporter MDR-1 (Pgp), the hERG cardiac channel, and the CYP3A4 enzyme.

| | In vitro Safety Assessment | | | | | |
|---|---|---|---|---|---|---|
| Compound | Inhibition of MDR1 ATPase EC50 [µM] | hERG Predictor EC50 [µM] | CYP3A4 Inhibition Testosteron EC50 [µM] | CYP3A4 Inhibition Testosteron Preincubation EC50 [µM] | CYP3A4 Inhibition Midazolam EC50 [µM] | CYP3A4 Inhibition Midazolam Preincubation EC50 [µM] |
| Cpd 3 | 38.6 | no inhibition | | | 3.2 | 0.98 |
| Cpd 4 | no full dose response | no full dose response | | | 3.9 | 2.3 |
| Cpd 6 | no inhibition | no inhibition | 34.3 | 1.4 | | |
| Cpd 5 | no inhibition | no full dose response | | | 3.8 | 1.2 |
| Cpd 7 | 1.08 | no inhibition | 27.0 | 1.1 | | |
| | | | Table 2B | | | |
| Cpd 50 WO07/ 020013 Cpd 1 | 6.95 | 8.17 | 6.3 | | 7.3 | 3 |
| Cpd 17 | no full dose response | 3.68 | 10.4 | 2.0 | | |
| Cpd 8 | 195.6 | no inhibition | 31.2 | 0.9 | | |
| Cpd 15 | 16.3 | | | | | |
| Cpd 9 | 0.836 | no full dose response | >10-30 | 1.5 | | |

Results depicted in bold letters are at least two fold improved with respect to the respective result obtained for compound 50 disclosed in WO07/020013.

In Vitro Microsomal Stability and Permeability (CaCo-2 Cells)

Metabolic stability in liver microsomes of different species (in the presence of NADPH, 1 mg/ml microsomal protein) was evaluated at 37° C. over time in triplicates at a test concentration of 10 µM. Loss of parent compound is measured by an HPLC-based UV detection method. For prediction of rat hepatic clearance half-lives ($t_{1/2}$) were fitted from first-order rate constant k ($min^{-1}$) obtained from the slope of time versus ln % remaining. Half-lives were used to calculate in vitro $CL_{int}$ and predict rat hepatic clearance by using following scaling factors for the rat: 44.8 mg microsomal protein/g liver, 40 g liver weight per kg of b.w., 55.2 ml/min/kg liver blood flow.

For the CaCo-2 permeability assay 80.000 CaCo-2 cells (ATCC HTB-37) were seeded in DMEM supplemented with 10% FCS, 1% Penicillin/Streptomycin and 1% non-essential amino acids per 24 well transwell plate (Corning 3397) and were grown for 21 days by changing the media every second day. On day 21 the medium was replaced by HBSS buffer (Invitrogen #14065) supplemented with 0.25% and 1% BSA for the donor and acceptor compartment, respectively. The compounds were added to the respective donor compartment in a concentration of 3 or 5 µM and were incubated for 2 hours at 37° C. The respective compound concentrations were determined by LC-MS analytics using an API 2000. Data analysis was performed as described by Sun and Pang 2008, Drug Metabolism and Disposition 36, 102-123.

TABLE 3

Shown in table 3A and 3B on the next two pages are the in vitro stability assessment results after incubation of the compounds with human liver microsomes in % remaining after 1 hour as well as the intestinal permeability prediction by measuring flux of the compounds through a CaCo-2 cell layer.

| | In vitro Stability Stability in Liver Microsomes | | | | In vitro Permeability | | |
|---|---|---|---|---|---|---|---|
| | Human | Rat | Dog | Mouse | CaCo-2 Assay | | |
| Compound | % Remaining after 1 h Incubation @37° C./1 mg/ml Liver Microsomes | | | | Papp [cm · s−1]. 10−6 ab | Papp [cm · s−1]. 10−6 ba | ba/ab |
| | | | | Table 3A | | | |
| Cpd 50 WO07/ 020013 | 28.6 | 39.2 | 36 | 0 | 0.1 | 15.58 | 155.8 |
| Cpd 3 | | 38.5 | | | 0.37 ± 0.02 | 17.19 ± 0.42 | 51.86 |
| Cpd 4 | 9.1 | 46.7 | | 0.0 (@30 min) | 1.41 +/− 0.07 | 25.39 +/− 1.09 | 18.04 |
| Cpd 6 | | 27.1 | | | | | |
| Cpd 5 | 0 | 41.9 | | 0.0 (@30 min) | 1.26 +/− 0.16 | 16.78 +/− 0.2 | 13.34 |

TABLE 3-continued

Shown in table 3A and 3B on the next two pages are the in vitro stability assessment results after incubation of the compounds with human liver microsomes in % remaining after 1 hour as well as the intestinal permeability prediction by measuring flux of the compounds through a CaCo-2 cell layer.

| | In vitro Stability | | | | In vitro Permeability | | |
|---|---|---|---|---|---|---|---|
| | Stability in Liver Microsomes | | | | CaCo-2 Assay | | |
| | Human | Rat | Dog | Mouse | | | |
| Compound | % Remaining after 1 h Incubation @37° C./1 mg/ml Liver Microsomes | | | | Papp [cm · s−1]. 10−6 ab | Papp [cm · s−1]. 10−6 ba | ba/ab |
| Cpd 7 | 82.7 | | | | | | |
| Table 3B | | | | | | | |
| Cpd 50 WO07/020013 Cpd 1 | 28.6 | 39.2 | 36 | 0 | 0.1 | 15.58 | 155.8 |
| Cpd 17 | 0 | 24.8 | | 0.0 (@30 min) | 22.41 +/− 5.7 | 10.04 +/− 2.45 | 0.45 |
| Cpd 8 | | 64.3 | | | 0.08 ± 0.08 | 0.74 ± 0.03 | 9.25 |
| Cpd 15 | | 37.8 | | | | | |
| Cpd 9 | | 54.8 | | | | | |

Results depicted in bold letters are at least two fold improved with respect to the respective result obtained for compound 50 disclosed in WO07/020013.

The invention claimed is:
1. A triazole compound, selected from the group consisting of:
  compound 1 [5-{(R)-2-(1H-Indol-3-yl)-1-[(pyridine-3-carbonyl)-amino]-ethyl}-4-(4-methoxy-benzyl)-4H-[1,2,4]triazol-3-yl]-acetic acid ethyl ester;
  compound 2 N-[(R)-1-[5-Carbamoylmethyl-4-(4-methoxy-benzyl)-4H-[1,2,4]triazol-3-yl]-2-(1H-indol-3-yl)-ethyl]-nicotinamide;
  compound 3 Pyridine-2-carboxylic acid [(R)-1-[5-[(R)-1-acetylamino-2-(1H-indol-3-yl)-ethyl]-4-(4-methoxy-benzyl)-4H-[1,2,4]triazol-3-yl]-2-(1H-indol-3-yl)-ethyl]-amide;
  compound 4 Pyridine-2-carboxylic acid [(R)-1-[5-((R)-1-acetylamino-2-phenyl-ethyl)-4-(4-methoxy-benzyl)-4H-[1,2,4]triazol-3-yl]-2-(1H-indol-3-yl)-ethyl]-amide;
  compound 5 Pyridine-2-carboxylic acid [(R)-1-[5-((R)-1-formylamino-2-phenyl-ethyl)-4-(4-methoxy-benzyl)-4H-[1,2,4]triazol-3-yl]-2-(1H-indol-3-yl)-ethyl]-amide;
  compound 6 N-[(R)-1-[5-((R)-1-Acetylamino-2-phenyl-ethyl)-4-(4-methoxy-benzyl)-4H-1,2,4]triazol-3-yl]-2-(1H-indol-3-yl)-ethyl]-2-hydroxy-acetamide;
  compound 7 (S)-Morpholine-2-carboxylic acid [(R)-1-[5-((R)-1-acetylamino-2-phenyl-ethyl)-4-(4-methoxy-benzyl)-4H-[1,2,4]triazol-3-yl]-2-(1H-indol-3-yl)-ethyl]amide;
  compound 8 N-[(R)-1-[5-[(R)-1-Acetylamino-2-(1H-indol-3-yl)-ethyl]-4-(4-methoxy-benzyl)-4H-[1,2,4]triazol-3-yl]-2-(1H-indol-3-yl)-ethyl]-2-amino-2-methyl-propionamide;
  compound 9 2-Amino-N-[(R)-1-[5-[(R)-1-formylamino-2-(1H-indol-3-yl)-ethyl]-4-(4-methoxy-benzyl)-4H-[1,2,4]-triazol-3-yl]-2-(1H-indol-3-yl)-ethyl]-2-methyl-propionamide;
  compound 10 N-[(R)-1-[5-((R)-1-Acetylamino-2-phenyl-ethyl)-4-(4-methoxy-benzyl)-4H-[1,2,4]triazol-3-yl]-2-(1H-indol-3-yl)-ethyl]-2-amino-2-methyl-propionamide;
  compound 11 Pyridine-2-carboxylic acid [(R)-1-[5-[1-acetylamino-2-(1H-indol-3-yl)-ethyl]-4-(4-methoxy-benzyl)-4H[1,2,4]triazol-3-yl]-2-(1H-indol-3-yl)-ethyl]-amide;
  compound 12 2-Amino-N-[(R)-1-[5-((R)-1-formylamino-2-phenyl-ethyl)-4-(4-methoxy-benzyl)-4H-[1,2,4]triazol-3-yl]-2-(1H-indol-3-yl)-ethyl]-2-methyl-propionamide;
  compound 13 Pyridine-2-carboxylic acid [(R)-1-[5-((S)-1-acetylamino-2-phenyl-ethyl)-4-(4-methoxy-benzyl)-4H-[1,2,4]triazol-3-yl]-2-(1H-indol-3-yl)-ethyl]-amide;
  compound 14 Pyridine-2-carboxylic acid [(R)-1-[5-[1-formylamino-2-(1H-indol-3-yl)-ethyl]-4-(4-methoxy-benzyl)-4H-[1,2,4]triazol-3-yl]-2-(1H-indol-3-yl)-ethyl]-amide;
  compound 15 {(R)-1-[5-[2-(1H-Indol-3-yl)-ethyl]-4-(4-methoxy-benzyl)-4H-[1,2,4]triazol-3-yl]-2-naphthalen-2-yl-ethyl}-carbamic acid tert-butyl ester;
  compound 16 1-{(R)-2-(1H-Indol-3-yl)-1-[4-(4-methoxy-benzyl)-5-phenethyl-4H-[1,2,4]triazol-3-yl]-ethyl}-3-isopropyl-urea;
  compound 17 {(R)-2-(1H-Indol-3-yl)-1-[4-(4-methoxy-benzyl)-5-phenethyl-4H-[1,2,4]triazol-3-yl]-ethyl}-carbamic acid isobutyl ester;
  compound 18 {(R)-2-(1H-Indol-3-yl)-1-[4-(4-methoxy-benzyl)-5-phenethyl-4H-[1,2,4]triazol-3-yl]-ethyl}-carbamic acid tert-butyl ester;
  compound 19 1-Benzyl-3-{(R)-2-(1H-indol-3-yl)-1-[4-(4-methoxy-benzyl)-5-phenethyl-4H-[1,2,4]triazol-3-yl]-ethyl}-urea;
  compound 20 1-Benzyl-3-{(R)-2-(1H-indol-3-yl)-1-[4-(4-methoxy-benzyl)-5-phenethyl-4H-[1,2,4]triazol-3-yl]-ethyl}-thiourea;
  compound 21 [(R)-1-[4-(4-Fluoro-benzyl)-5-phenethyl-4H-[1,2,4]triazol-3-yl]-2-(1H-indol-3-yl)-ethyl]-carbamic acid tert-butyl ester;
  compound 22 {(R)-2-(1H-Indol-3-yl)-1-[4-(4-isopropoxy-benzyl)-5-phenethyl-4H-[1,2,4]triazol-3-yl]-ethyl}-carbamic acid tert-butyl ester;

compound 23 {(R)-2-(1H-Indol-3-yl)-1-[4-(4-methoxy-benzyl)-5-phenethyl-4H-[1,2,4]triazol-3-yl]-ethyl}-methyl-carbamic acid tert-butyl ester;

compound 24 [(R)-1-[4-(2,4-Dimethoxy-benzyl)-5-phenethyl-4H-[1,2,4]triazol-3-yl]-2-(1H-indol-3-yl)-ethyl]-carbamic acid tert-butyl ester;

compound 25 Piperidine-4-carbothioic acid {(R)-2-(1H-indol-3-yl)-1-[4-(4-methoxy-benzyl)-5-phenethyl-4H-[1,2,4]triazol-3-yl]-ethyl}-amide;

compound 26 2-Amino-N-{(R)-2-(1H-indol-3-yl)-1-[4-(4-methoxy-benzyl)-5-phenethyl-4H-[1,2,4]triazol-3-yl]-ethyl}-thioacetamide;

compound 27 Pyridine-2-carbothioic acid {(R)-2-(1H-indol-3-yl)-1-[4-(4-methoxy-benzyl)-5-phenethyl-4H-[1,2,4]-triazol-3-yl]-ethyl}-amide;

and a physiologically tolerated salt thereof.

2. A pharmaceutical composition, comprising a pharmacologically active amount of at least one compound of claim 1.

3. The pharmaceutical composition of claim 2, wherein an active ingredient is present in a unit dose of from 0.001 mg to 100 mg per kg of a patient's bodyweight.

4. The pharmaceutical composition of claim 2, further comprising at least one selected from the group consisting of a pharmaceutically acceptable carrier and a pharmaceutically acceptable excipient.

5. The pharmaceutical composition of claim 2, further comprising at least one further pharmacologically active substance.

6. The pharmaceutical composition of claim 5, wherein the further pharmacologically active substance is an endocannabinoid receptor antagonist.

* * * * *